United States Patent [19]

Udodong et al.

[11] Patent Number: 6,043,341
[45] Date of Patent: Mar. 28, 2000

[54] CYCLIC PEPTIDE ANTIFUNGAL AGENTS

[75] Inventors: Uko Effiong Udodong; John Leo Grutsch, Jr.; Marvin Martin Hansen; Allen Robert Harkness, all of Indianapolis; Daniel Edward Verral, II, Clinton, all of Ind.

[73] Assignee: Eli Lilly & Co., Indianapolis, Ind.

[21] Appl. No.: 09/129,062

[22] Filed: Aug. 4, 1998

Related U.S. Application Data

[60] Provisional application No. 60/054,538, Aug. 4, 1997.
[51] Int. Cl.[7] .............................. A61K 38/12; C07F 9/32; C07K 7/56
[52] U.S. Cl. .............................. 530/317; 514/7; 530/345; 558/152
[58] Field of Search ..................... 514/7, 9, 11; 530/317, 530/345; 558/152

[56] References Cited

U.S. PATENT DOCUMENTS

| | | | |
|---|---|---|---|
| 2,632,768 | 3/1953 | Coover, Jr. et al. | 558/152 |
| 5,359,115 | 10/1994 | Campbell et al. | 558/110 |
| 5,646,111 | 7/1997 | Borromeo et al. | 514/11 |
| 5,786,325 | 7/1998 | Borromeo et al. | 514/11 |

OTHER PUBLICATIONS

*J. Med. Chem.,* Balkovec, et al. (1992) vol. 35, 194–198.

*Primary Examiner*—Jeffrey E. Russel
*Attorney, Agent, or Firm*—Morrison & Foerster, LLP

[57] ABSTRACT

The present invention provides phosphonylating agents and phosphonylation conditions that are compatible with the acid- and base-sensitive compounds and which promote a regioselective and reproducible conversion to a phosphonate compound. Also provided are intermediates that may be used to prepare phosphonate derivatives of cyclic peptides antifungal agent and a process for converting the phosphonates to the desired phosphonic acid prodrugs.

21 Claims, No Drawings

CYCLIC PEPTIDE ANTIFUNGAL AGENTS

This application claims the benefit of U.S. Provisional Application No. 60/054,538, filed Aug. 4, 1997.

FIELD OF THE INVENTION

The present invention is in the field of organic chemistry. Specifically, the present invention provides phosphonylating agents and conditions that may be used to prepare phosphonate derivative.

BACKGROUND OF THE INVENTION

This invention relates to a phosphonylating agent and phosphonylation conditions that are mild and promote a regioselective, reproducible conversion of an hydroxy moiety to the corresponding phosphonate derivative. The phosphonylating agents and conditions may be used for preparing derivatives of pharmaceutical compounds which have improved stability and water solubility. For example, this invention may be used to make derivatives of various cyclic peptide compounds which are used as antifungal and antiparasitic agents.

In general, the cyclic peptides are unstable under basic conditions. Specifically, the presence of a base causes ring opening and decomposition of the cyclic peptide. In addition, the cyclic peptides are sensitive to strong acids. A popular strategy for phosphonylating the hydroxy moiety of a compound involves the use of an alkyl phosphonic dichloride as the phosphonylating agent. However, a by-product of the hydrolytic work-up of the reaction is hydrochloric acid. The reaction is typically carried out in the presence of a base which both promotes the phosphonylation reaction and acts as an acid scavenger. This reaction has limited usefulness with respect to the cyclic peptides as a result of poor yields due to the sensitivity of the nucleus to both base and acid. In addition, alkyl phosphonic dichloride reagents are very reactive and not regioselective for reaction at only the desired phenolic oxygen of the polyfunctional cyclic peptides.

The cyclic peptides are produced by fermentation of various microorganisms. A number of cyclic peptides are known in the art including echinocandin B (A30912A), aculeacin, mulundocandin, sporiofungin, L-671,329, and S31794/F1. In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain. The fatty acid side chains may be removed from the cyclic peptide core to provide an amino nucleus (for example, a compound of formula II, below, where $R_2$ is hydrogen). The amino group may then be re-acylated to provide semi-synthetic compounds which may be phosphonylated according to the present invention.

Examples of echinocandin compounds that may be converted to the corresponding phosphonate derivatives include compounds of formula IIB:

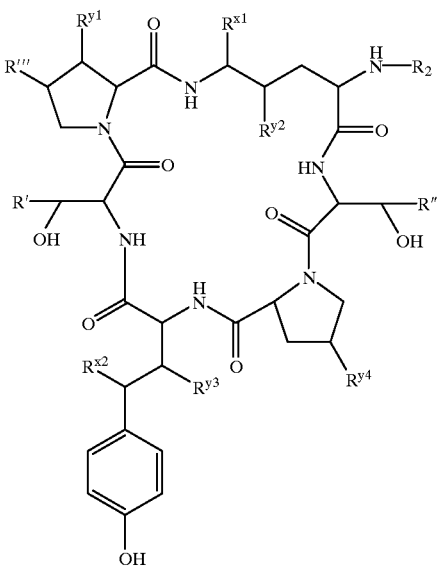

wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$, and $R^{y4}$ are independently hydroxy or hydrogen; and $R_2$ is an acyl side chain as defined herein.

Such cyclic peptides are useful antifungal and antiparasitic agents due to their biological activity against these pathogens. These compounds may be used as oral, topical or intravenous (iv) drugs. However, these compounds are not well-suited for intravenous formulation due to their relatively poor aqueous solubility. Yet, an iv formulation is particularly desirable when the drug is to be used with a patient who is unable to take it orally, for example because the patient is immunocompromised, or when it is necessary to obtain high levels of compound systemically, for example when treating a systemic infection, an organ infection such as hepatosplenic infection or an iv catheter candida infection.

The development of an antifungal or antiparasitic drug using these compounds necessitates increasing the aqueous solubility of the compounds using either formulation technology or by the development of a suitable prodrug. With respect to the latter, it has been discovered that the phosphonic acid derivatives of the various cyclic peptides have properties that are desirable for effective prodrugs. Specifically, the echinocandins may be converted to a phosphonic acid prodrug by phosphonylating the phenolic hydroxy of the homotyrosine moiety and then deprotecting the resultant phosphonate to provide the desired phosphonic acid derivative.

The present invention provides a phosphonylating agent and phosphonylation conditions that are compatible with the sensitive cyclic peptide nucleus and promote a clean and reproducible conversion to a phosphonate derivative. The phosphonylation conditions are selective for phosphonylation at the homotyrosine moiety.

The present invention also provides intermediate compounds useful in preparing the phosphonate derivatives of these cyclic peptides and a process for preparing the desired phosphonic acid derivatives.

SUMMARY OF THE INVENTION

The present invention provides a compound of formula I:

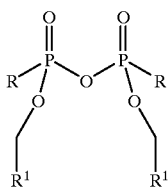

I where:

R is $C_1$–$C_6$ alkyl, phenyl or benzyl;

$R^1$ is phenyl, naphthyl, cyclohexyl or a compound of the formula

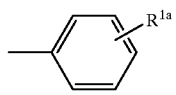

where $R^{1a}$ is hydrogen, halo, trifluoromethyl, $C_1$–$C_6$ alkyl, $C_1$–$C_6$ alkoxy, hydroxy, cyano, nitro, protected amino, phenyl, benzyl or benzyloxy; with the proviso that when $R^1$ is

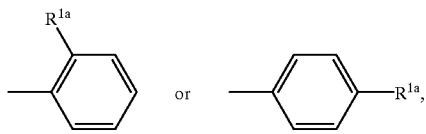

then $R^{1a}$ cannot be hydroxy, $C_1$–$C_6$ alkoxy or benzyloxy; or a pharmaceutically acceptable salt thereof Also provided is a compound of formula II

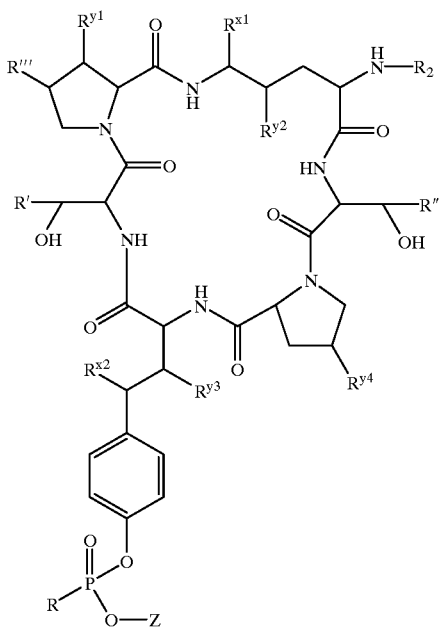

II wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$, and $R^{y4}$ are independently hydroxy or hydrogen;

R is $C_1$–$C_6$ alkyl, phenyl or benzyl;

Z is —$CH_2$—$R^1$;

$R^1$ is phenyl, naphthyl, cyclohexyl or a compound of the formula

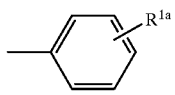

where $R^{1a}$ is hydrogen, halo, trifluoromethyl, $C_1$–$C_6$ alkyl, $C_1$–$C_6$ alkoxy, hydroxy, cyano, nitro, protected amino, phenyl, benzyl or benzyloxy;

$R_2$ is acyl;

with the proviso that when $R^1$ is

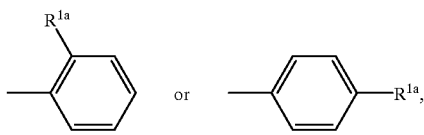

then $R^{1a}$ cannot be hydroxy, $C_1$–$C_6$ alkoxy or benzyloxy; or a pharmaceutically acceptable salt thereof.

The present invention further provides a process for preparing a compound of formula IIA

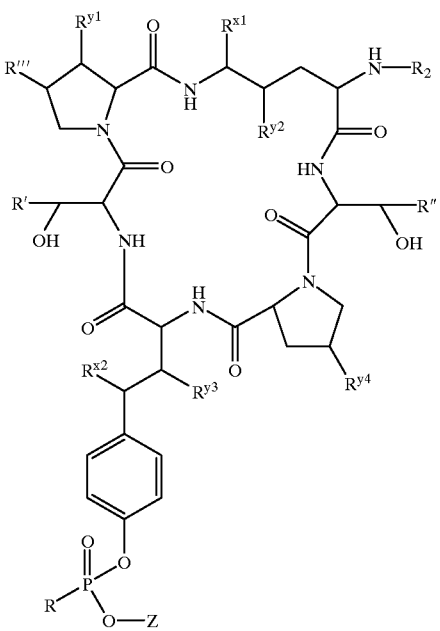

IIA wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$ and $R^{y4}$ are independently hydroxy or hydrogen;

R is $C_1$–$C_6$ alkyl, phenyl or benzyl;

Z is hydrogen or —CH$_2$—R$^1$;

R$^1$ is phenyl, naphthyl, cyclohexyl or a compound of the formula

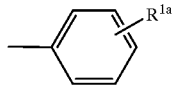

where R$^{1a}$ is hydrogen, halo, trifluoromethyl, C$_1$–C$_6$ alkyl, C$_1$–C$_6$ alkoxy, hydroxy, cyano, nitro, protected amino, phenyl, benzyl or benzyloxy;

R$_2$ is acyl;

with the proviso that when R$^1$ is

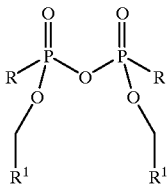

then R$^{1a}$ cannot be hydroxy, C$_1$–C$_6$ alkoxy or benzyloxy; or a pharmaceutically acceptable salt thereof; which comprises a) reacting a compound of formula I

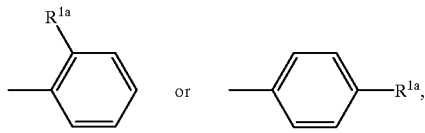

with a compound of formula IIB

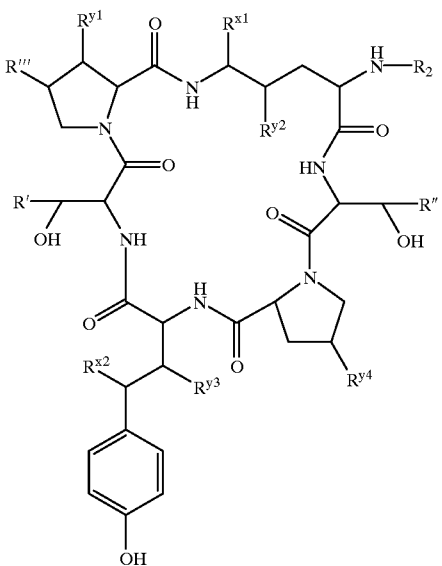

in the presence of a base at a temperature of from about −30° C. to about 40° C. to provide a compound of formula II;

b) optionally converting the compound of formula II to provide the compound of formula IIA where Z is hydrogen; and c) optionally forming a pharmaceutically acceptable salt.

The present invention further provides a process for converting a compound of formula II:

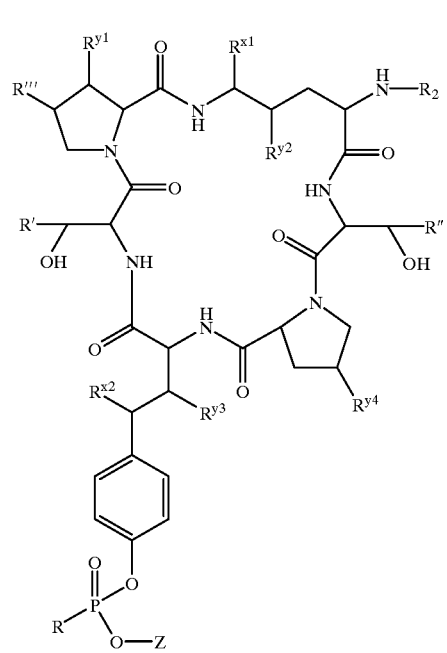

wherein:

R' is hydrogen, methyl or NH$_2$C(O)CH$_2$—;

R" and R''' are independently methyl or hydrogen;

R$^{x1}$, R$^{x2}$, R$^{y1}$, R$^{y2}$, R$^{y3}$, and R$^{y4}$ are independently hydroxy or hydrogen;

R is C$_1$–C$_6$ alkyl, phenyl or benzyl;

Z is —CH$_2$—R$^1$;

R$^1$ is phenyl, naphthyl, cyclohexyl or a compound of the formula where R$^{1a}$ is hydrogen, halo, trifluoromethyl, C$_1$–C$_6$ alkyl, C$_1$–C$_6$ alkoxy, hydroxy, cyano, nitro, protected amino, phenyl, benzyl or benzyloxy;

R$_2$ is acyl;

with the proviso that when R$^1$ is then R$^{1a}$ cannot be hydroxy, C$_1$–C$_6$ alkoxy or benzyloxy; or a pharmaceutically acceptable salt thereof; to a compound of formula IIA:

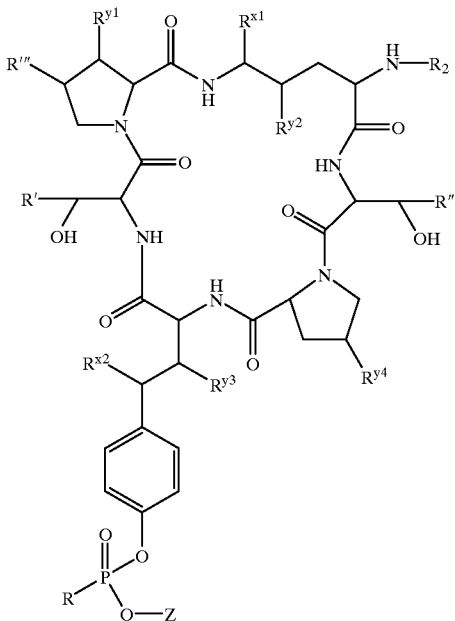

where:

R', R", R'", $R^{x1}$, $R^{x2}$, $R^{y1}$, $R^{y2}$, $R^{y3}$, $R^{y4}$, R and $R_2$ are as defined above; and Z is hydrogen, which comprises 1) hydrogenating the compound of formula II by
   a) exposure to hydrogen gas in the presence of a catalyst and a base; or
   b) reaction with an alkali metal in liquid ammonia; and
2) optionally forming a pharmaceutically acceptable salt.

DETAILED DESCRIPTION

As used herein, the term "acyl" refers to the substituent, $R_2$ in a compound of formula II, above:

I) $R_2$ is a Group of the Formula

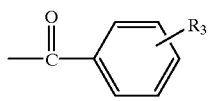

where:

A) $R_3$ is $C_1$–$C_{12}$ alkyl, $C_1$–$C_6$ alkoxy or quinolyl;
B) $R_3$ is —O—$(CH_2)_m$—[O—$(CH_2)_n$]$_p$—O—($C_1$–$C_{12}$ alkyl);
   m and n are independently 2, 3 or 4;
   p is 0 or 1; or
C) $R_3$ is —Y—($C_1$–$C_{12}$ alkyl);
   Y is —C≡C— or —CH=CH—; or
D) $R_3$ is —O—$(CH_2)_q$—G;
   q is 2, 3 or 4;
   G is $C_7$–$C_{10}$ bicycloalkyl or $C_7$–$C_{14}$ tricycloalkyl; or II) $R_2$ is a group of the formula

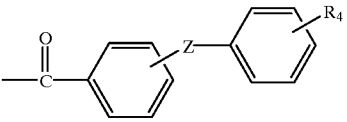

where:
Z is —O—, —C≡C—, —CH=CH—, —$CH_2$—$CH_2$—, —$CH_2$— or a bond;
A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or
B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or phenyl substituted with a group of the formula —O—$(CH_2)_m$—[O—$(CH_2)_n$]$_p$—O—($C_1$–$C_{12}$ alkyl) where m, n and p are as defined above; or
C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula —O—$(CH_2)_m$—[O—$(CH_2)_n$]$_p$—O—($C_1$–$C_{12}$ alkyl) where m, n and p are as defined above; or
D) $R_4$ is —O—$(CH_2)_r$—W—$R_5$;
   r is 2, 3 or 4;
   W is pyrrolidino, piperidino or piperazino;
   $R_5$ is hydrogen, $C_1$–$C_{12}$ alkyl, $C_3$–$C_{12}$ cycloalkyl, benzyl or $C_3$–$C_{12}$ cycloalkylmethyl; or
E) $R_4$ is —$Y^1$—$R_6$;
   $Y^1$ is —C≡C— or —CH=CH—;
   $R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—$(CH_2)_r$—W—$R_5$ where r, W and $R_5$ are as defined above; or
   $R_6$ is phenyl substituted with a group of the formula —O—$(CH_2)_m$—[O—$(CH_2)_n$]$_p$—O—($C_1$–$C_{12}$ alkyl) where m, n and p are as defined above; or
F) $R_4$ is $C_1$–$C_{12}$ alkoxy substituted with a group of the formula —NHC(O)$R_7$;
   $R_7$ is $C_1$–$C_6$ alkoxy, or phenyl($C_1$–$C_6$ alkoxy); or III) $R_2$ is a Group of the Formula

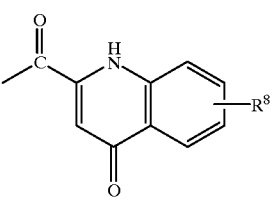

where $R^8$ is $C_1$–$C_{12}$ alkoxy or a group of the formula —O—$(CH_2)_m$—[O—$(CH_2)_n$]$_p$—O—($C_1$–$C_{12}$ alkyl) where m, n and p are as defined above; or IV) R$_2$ is a Group of the Formula

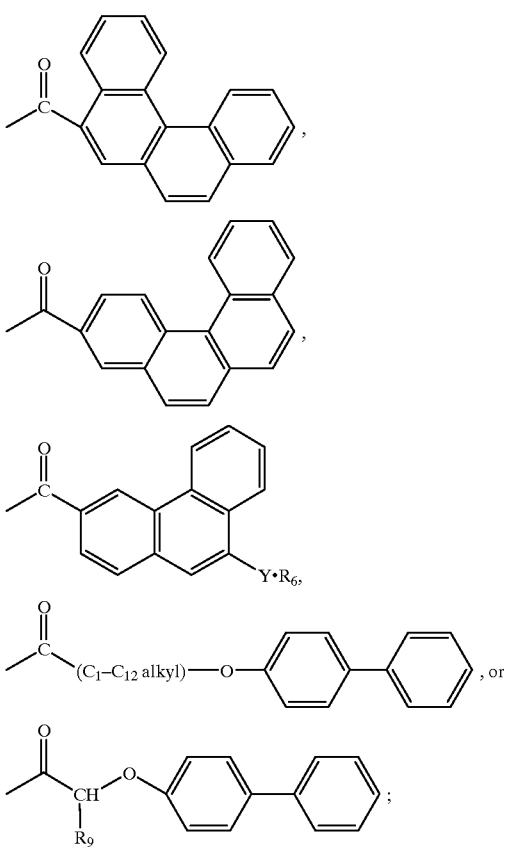

where:

Y and R$_6$ are as defined above;

R$_9$ is phenyl, C$_1$–C$_{12}$ alkyl, or C$_1$–C$_{12}$ alkoxy; or

V) R$_2$ is Naphthoyl Substituted with R$_4$ where R$_4$ is as Defined Above.

The term "C$_1$–C$_{12}$ alkyl" refers to a straight or branched alkyl chain having from 1 to 12 carbon atoms. Typical C$_1$–C$_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "C$_1$–C$_{12}$ alkyl" includes within its definition the terms "C$_1$–C$_6$ alkyl" and C$_1$–C$_4$ alkyl."

The term "halo" refers to chloro, fluoro, bromo or iodo.

The term "C$_2$–C$_{12}$ alkenyl" refers to a straight or branched alkenyl chain having from 2 to 12 carbon atoms. Typical C$_2$–C$_{12}$ alkenyl groups include ethenyl, 1-propen-2-yl, 3-buten-1-yl, 1-buten-2-yl, 1-buten-1-yl, 1-penten-3-yl, 2-hexen-3-yl, 1-decen-2-yl, 2-decen-5-yl and the like.

The term "C$_2$–C$_{12}$ alkynyl" refers to a straight or branched alkynyl chain having from 2 to 12 carbon atoms. Typical C$_2$–C$_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "C$_1$–C$_{12}$ alkylthio" refers to a straight or branched alkyl chain having from 1 to 12 carbon atoms attached to a sulfur atom. Typical C$_1$–C$_{12}$ alkylthio groups include methylthio, ethylthio, propylthio, isopropylthio, butylthio, 3-methyl-heptylthio, octylthio, 5,5-dimethylhexylthio and the like.

The term "C$_1$–C$_{12}$ alkoxy" refers to a straight or branched alkyl chain having from 1 to 12 carbon atoms attached to an oxygen atom. Typical C$_1$–C$_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "C$_1$–C$_{12}$ alkyl" includes within its definition the terms "C$_1$–C$_6$ alkoxy" and "C$_1$–C$_4$ alkoxy."

The terms "C$_1$–C$_{12}$ substituted alkyl," "C$_2$–C$_{12}$ substituted alkenyl" and "C$_2$–C$_{12}$ substituted alkynyl," refers to the specified moiety substituted with 1 or 2 substituents independently selected from halo, hydroxy, protected hydroxy, amino, protected amino, C$_1$–C$_7$ acyloxy, nitro, carboxy, protected carboxy, carbamoyl, carbamoyloxy, cyano, methylsulfonylamino, phenyl, substituted phenyl or C$_1$–C$_{12}$ alkoxy.

The term "substituted phenyl" refers to a phenyl group substituted with 1, 2 or 3 substituents independently selected from halo, hydroxy, protected hydroxy, cyano, nitro, C$_1$–C$_{12}$ alkyl, C$_1$–C$_{12}$ alkoxy, carboxy, protected carboxy, carboxymethyl, hydroxymethyl, amino, aminomethyl, trifluoromethyl or N-methylsulfonylamino.

The term "C$_3$–C$_{12}$ cycloalkyl" refers to a saturated hydrocarbon ring structure having from 3 to 12 carbon atoms. Typical C$_3$–C$_{12}$ cycloalkyl groups include cyclopropyl, cyclobutyl, cyclopentyl, cyclohexyl and cycloheptyl, cyclooctyl and the like.

The term "C$_3$–C$_{12}$ cycloalkoxy" refers to a C$_3$–C$_{12}$ cycloalkyl group attached to an oxygen atom. Typical C$_3$–C$_{12}$ cycloalkoxy groups include cyclopropyloxy, cyclobutyloxy, cyclopentyloxy, cyclohexyloxy and cycloheptyloxy and the like.

The term "C$_3$–C$_{12}$ cycloalkenyl" refers to a hydrocarbon ring structure having from 3 to 12 carbon atoms with at least one double bond. Typical C$_3$–C$_{12}$ cycloalkenyl groups include cyclopropenyl, cyclobutenyl, cyclopentenyl and the like.

The term "methyl (C$_3$–C$_{12}$ cycloalkyl)" refers to a C$_3$–C$_{12}$ cycloalkyl group that is substituted with a methyl group. Typical methyl(C$_3$–C$_{12}$ cycloalkyl) groups include 2-methylcycloproyl, 2-methylcyclobutyl, 3-methylcyclopentyl, 4-methylcyclohexyl and the like.

The term "C$_1$–C$_4$ alkylamino" refers to a straight or branched alkylamino chain having from 1 to 4 carbon atoms attached to a nitrogen atom. Typical C$_1$–C$_4$ alkylamino groups include methylamino, ethylamino, propylamino, isopropylamino, butylamino, sec-butylamino and the like.

The term "di(C$_1$–C$_4$ alkyl)amino" refers to a di(C$_1$–C$_4$ alkyl)amino chain having two straight or branched alkyl chains of from 1 to 4 carbon atoms attached to a common nitrogen atom. Typical di(C$_1$–C$_4$ alkyl)amino groups include dimethylamino, diethylamino, ethylmethylamino, methylisopropylamino, dipropylamino, dibutylamino, methylbutylamino, t-butylisopropylamino, di-t-butylamino and the like.

The term "C$_2$–C$_{12}$ alkanoyl" represents a straight or branched alkyl chain having from 1 to 4 carbon atoms attached to a carbonyl moiety. Typical C$_2$–C$_{12}$ alkanoyl groups include ethanoyl, propanoyl, isopropanoyl, butanoyl, isobutanoyl, sec-butanoyl, t-butanoyl, pentanoyl and the like.

The term "C$_2$–C$_{12}$ alkanoylamino" represents a straight or branched alkyl chain attached to a carbonylamino moiety. Typical C$_2$–C$_{12}$ alkanoylamino groups include ethanoylamino, propanoylamino, isopropanoylamino, butanoyl-amino, isobutanoylamino, sec-butanoylamino, t-butanoylamino, pentanoylamino and the like.

The terms "C$_7$–C$_{10}$ bicycloalkyl" represents two fused cycloalkyl rings having a total of 7 to 10 carbon atoms and "$C_7$–$C_{14}$ tricycloalkyl" represents 3 fused cycloalkyl rings having a total of 7 to 14 carbon atoms. Typical "$C_7$–$C_{10}$ bicycloalkyl" and "$C_7$–$C_{14}$ tricycloalkyl" groups include bicyclo[2.2.1.]hept-2-yl, bicyclo[2.2.1.]hept-4-en-2-yl, bicyclo[3.3.1.]non-3-yl, bicyclo[3.3.1.]non-2-yl, bicyclo[3.2.1.]oct-2-yl, bicyclo[2.2.2.]oct-2-yl, bicyclo[2.2.2]oct-5-en-2-yl, adamantyl and the like.

Preferred acyl groups, $R_2$, include groups of the formula:

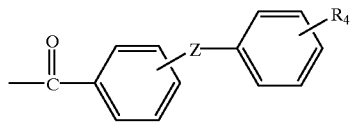

wherein:

Z is —C≡C—, —CH=CH—, —CH$_2$—CH$_2$—, or a bond;

A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or a group of the formula —O—(CH$_2$)$_m$—[O—(CH$_2$)$_n$]$_p$—O—($C_1$–$C_{12}$ alkyl) where m, n and p are as defined above; or C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino formamido, $C_2$–$C_{12}$ alkanoylamino, or phenyl substituted with a group of the formula —O—(CH$_2$)$_m$—[O—(CH$_2$)$_n$]$_p$—O—($C_1$–$C_{12}$ alkyl) where m, n and p are as defined above; or D) $R_4$ is —O—(CH$_2$)$_r$—W—$R_5$;
   r is 2, 3 or 4;
   W is pyrrolidino, piperidino or piperazino;
   $R_5$ is hydrogen, $C_1$–$C_{12}$ alkyl, $C_3$–$C_{12}$ cycloalkyl, benzyl or $C_3$–$C_{12}$ cycloalkylmethyl; or E) $R_4$ is —Y$^1$—$R_6$;
   Y$^1$ is —C≡C— or —CH=CH—;
   $R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula —O—(CH$_2$)$_r$—W—$R_5$ where r, W and $R_5$ are as defined above; or
   $R_6$ is phenyl substituted with a group of the formula —O—(CH$_2$)$_m$—[O—(CH$_2$)$_n$]$_p$—O—($C_1$–$C_{12}$ alkyl) where m, n and p are as defined above; or F) $R_4$ is $C_1$–$C_{12}$ alkoxy substituted with a group of the formula —NHC(O)$R_7$;
   $R_7$ is $C_1$–$C_6$ alkoxy, or phenyl($C_1$–$C_6$ alkoxy). More preferred are acyl groups, $R_2$, of the formula:

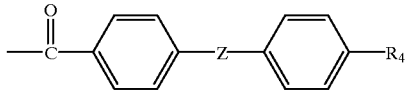

where Z is —CO≡C— or a bond;
or a pharmaceutically acceptable salt thereof.

The following acyl groups, $R_2$, are preferred:

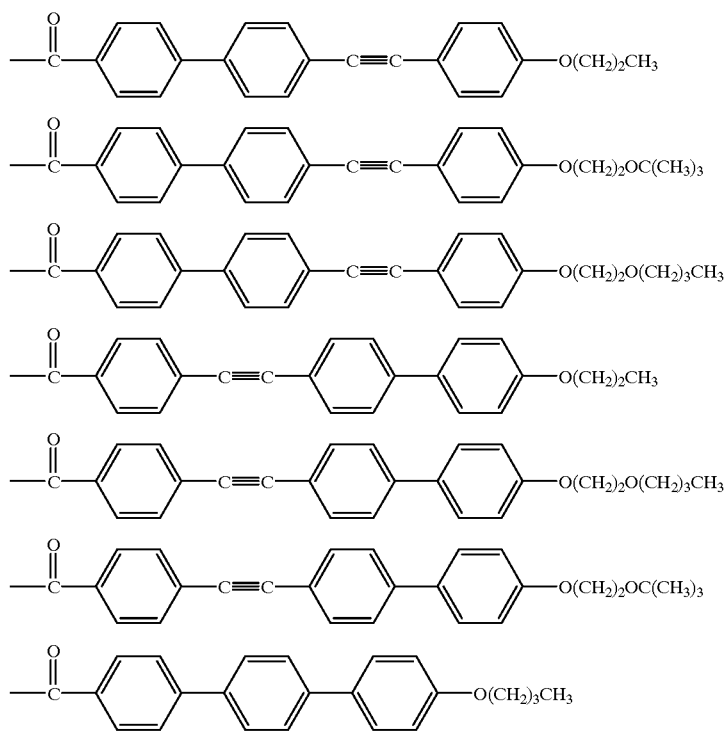

-continued

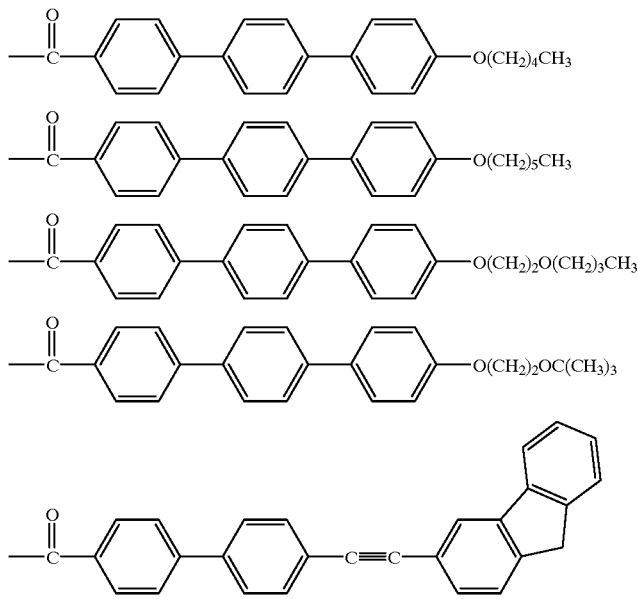

The term "hydroxy-protecting group" refers to a substituent of an hydroxy group that is commonly employed to block or protect the hydroxy functionality while reactions are carried out on other functional groups on the compound. Examples of such hydroxy-protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4''-trimethoxytrityl, benzyl, allyl, trimethylsilyl, (t-butyl)dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy-protecting group is trimethylsilyl. Further examples of hydroxy-protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy-protecting groups.

The term "dideoxy" refers to compounds of the formula IIB where $R^{x1}$ and $R^{x2}$ are each hydrogen.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methane sulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of formula I are those compounds where:

R is $C_1$–$C_4$ alkyl;

$R^1$ is phenyl or a compound of the formula

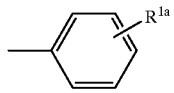

where $R^{1a}$ is hydrogen, halo, $C_1$–$C_6$ alkyl or $C_1$–$C_6$ alkoxy; or a pharmaceutically acceptable salt thereof.

Of these compounds, more preferred compounds of formula I are those compounds where:

R is methyl;

$R^1$ is phenyl or a compound of the formula

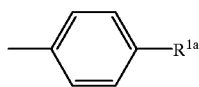

where $R^{1a}$ is halo or hydrogen;

or a pharmaceutically acceptable salt thereof.

Further preferred compounds are those compounds of formula I where:

$R^1$ is phenyl or a compound of the formula

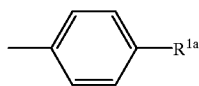

where $R^{1a}$ is bromo or hydrogen;

or a pharmaceutically acceptable salt thereof.

The compounds of formula I may be prepared by self-coupling the corresponding phosphonic acid of formula Ia

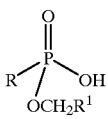

where $R^1$ is defined in claim 1, in an aprotic solvent at a temperature of from about 0° C. to about 60° C. and in the presence of a coupling agent.

The phosphonic acid Ia is inherently racemic due to the following tautomeric equilibrium:

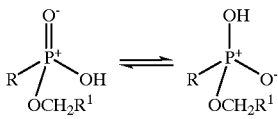

When the tautomers are coupled, they provide a mixture of syn and anti diastereomers:

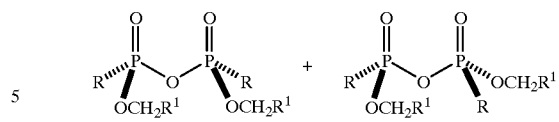

The reaction is typically carried out for about 30 minutes to about 24 h at a temperature of from about 15° C. to about 40° C., preferably for about 30 minutes to about 2 h at room temperature. Typical solvents for this reaction include aprotic solvents such as tetrahydrofuran (THF), ethyl acetate (EtOAc), toluene or methylene chloride ($CH_2Cl_2$) or a mixture of such solvents. A preferred solvent mixture is one formed from EtOAc and $CH_2Cl_2$, preferably in a ratio of 5:1 of EtOAc to $CH_2Cl_2$. Solvent choice is not critical so long as the solvent employed is inert to the ongoing reaction and the reactants are sufficiently solubilized to effect the desired reaction. Typical coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazol-1-yloxytripyrrolidino-phosphonium hexafluorophosphate (PyBOP) and the like. A preferred coupling agent is DCC.

The pyrophosphonates prepared in the coupling reaction described above are obtained as a mixture of syn and anti diastereomers. The diastereomers may be separated using procedures known in the art. For example, they may be separated by selective recrystallization from a suitable solvent or solvent mixture. A preferred solvent mixture is a mixture of hexanes and EtOAc. Either diastereomeric form or the diastereomeric mixture may be used as a phosphonylating agent.

The pyrophosphonate compounds, the mixture of pyrophosphonate diastereomers or any of the intermediate compounds used to prepare such pyrophosphonates may be isolated by procedures well-known in the art. For example, once a reaction is complete, the desired compound may be crystallized and then collected by filtration, or the reaction solvent may be removed by evaporation or decantation. The desired compound may also be isolated from the reaction mixture by extraction. The intermediate compound may be further purified, if desired, by common techniques such as crystallization or chromatography over solid supports such as silica gel, alumina and the like, before carrying out the next step of the reaction scheme.

The compounds of formula Ia may be prepared according to Reaction Scheme I, as follows.

Reaction Scheme I

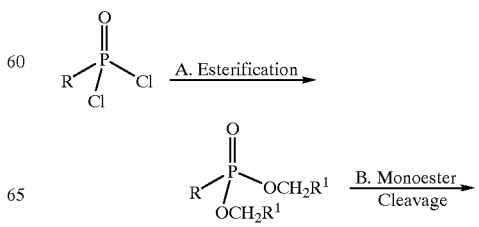

-continued

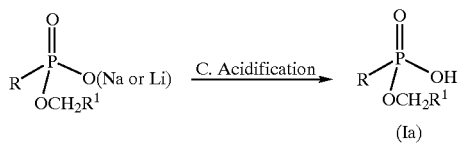

(Ia)

Reaction scheme I, above, is accomplished by carrying out reactions A-C, in order.

In reaction IA, a suitably substituted phosphonic acid dihalide is esterified by reaction with an appropriately substituted alcohol, preferably in the presence of a base. Preferred phosphonic acid dihalides used in this reaction are the dichlorides. The reaction is typically carried out with 2–4 equivalents of the alcohol relative to the phosphonic acid dihalide at a temperature of from about −40° C. to about 25° C. Suitable solvents for this reaction include solvents such as THF, diethyl ether (Et$_2$O), methyl-t-butylether (MTBE) or CH$_2$Cl$_2$, preferably Et$_2$O or MTBE. Solvent choice is not critical so long as the solvent employed is inert to the ongoing reaction and the reactants are sufficiently solubilized to effect the desired reaction. Typical bases include triethylamine (Et$_3$N), N-methyl-morpholine (NMM) and diisopropylethylamine. A preferred base is diisopropylethylamine in the presence of a catalytic amount of 1H-tetrazole. The reaction is generally complete in about 3 to 5 hours when carried out at a temperature of from about 0° C. to about 25° C.

In reaction IB, one of the ester groups on the diester compound obtained from reaction IA is selectively cleaved by reaction with sodium iodide (NaI) or lithium iodide (LiI) in a suitable solvent to provide the corresponding monoester compound. The reaction is typically carried out with 1 to 3 equivalents of the iodide relative to the diester compound at a temperature of from about −20° C. to the reflux temperature of the mixture. Suitable solvents for this reaction include solvents such as acetone, dimethylformamide (DMF), EtOAc, CH$_2$Cl$_2$ and the like. A preferred solvent is acetone. Solvent choice is not critical so long as the solvent employed is inert to the ongoing reaction and the reactants are sufficiently solubilized to effect the desired reaction.

In reaction IC, the monoester compound obtained from reaction IB is converted to the desired phosphonic acid Ia by treatment with an aqueous acid. Typical acids include any inorganic acid such as HCl, hydrobromic acid or sulfuric acid. A preferred acid is HCl. The acid is typically used in a concentration of about 0.1 molar (0.1M) to about 12M, preferably about 6M.

An alternate synthesis of the phosphonic acid Ia is by direct monochloride displacement of a phosphonic acid dihalide with a suitably substituted alcohol of the formula R$^1$—CH$_2$OH at a temperature of from about −40° C. to about 25° C. in a suitable organic solvent such as THF, Et$_2$O, MTBE or CH$_2$Cl$_2$. The reaction is preferably carried out in the presence of a base. The reaction is generally carried out with an equimolar amount to about a two times excess of the phosphonic acid dihalide relative to the alcohol. Solvent choice is not critical so long as the solvent employed is inert to the ongoing reaction and the reactants are sufficiently solubilized to effect the desired reaction. Typical bases include, Et$_3$N, N-methylmorpholine (NMM), diisopropylethylamine or 1H-tetrazole. The reaction is generally complete in about 90 minutes when carried out at a temperature in the range of 0–5° C.

The reaction may be quenched by the addition of water and a base such as an hydroxide such as sodium hydroxide (NaOH), potassium hydroxide (KOH), lithium hydroxide (LiOH), or Et$_3$N, diisopropylethylamine or NMM which results in a mixture of the desired pyrophosphonate and the corresponding phosphonic acid monoester Ia. Since some phosphonic diester is formed in the reaction mixture, it is preferable to hydrolyze the pyrophosphonate to the corresponding phosphonic monoester by stirring the pyrophosphonate for about 8 to about 36 h in the presence of an aqueous base to hydrolyze the pyrophosphonate compound to the phosphonic acid monoester Ia (such as is isolated above in Reaction IC). Typical bases include the hydroxides such as NaOH, KOH, LiOH or calcium hydroxide. The desired phosphonic acid Ia may be easily separated from the phosphonic acid diester by extraction.

The naturally-occurring cyclic peptides used in the present invention may be prepared by fermentation of known microorganisms. For example, the cyclic peptide of formula IIB where R', R" and R"' are methyl, R$^{x1}$ and R$^{x2}$ are hydroxy, R$^{y1}$, R$^{y2}$, R$^{y3}$, R$^{y4}$ are hydroxy and R$_2$ is linoleoyl (cyclic peptide corresponding to A-30912A) may be prepared using the procedure detailed in Abbott et al., U.S. Pat. No. 4,293,482, which is herein incorporated by reference. The nucleus of formula IIB where R', R", and R"' are methyl, R$^{x1}$ is hydroxy, R$^{x2}$ is hydrogen, R$^{y1}$, R$^{y2}$, R$^{y3}$, R$^{y4}$ are hydroxy and R$_2$ is linoleoyl (nucleus corresponding to A-30912B) may be prepared using the procedure detailed in Abbott et al., U.S. Pat. No. 4,299,763, which is herein incorporated by reference. The cyclic peptide of formula IIB where R', R", and R"' are methyl, R$^{x1}$ and R$^{x2}$ are hydrogen, R$^{y1}$, R$^{y3}$ and R$^{y4}$ are hydroxy, R$^{y2}$ is hydrogen and R$_2$ is linoleoyl (nucleus corresponding to A-30912D) may be prepared using the procedure detailed in Abbott et al., U.S. Pat. No. 4,299,762, which is herein incorporated by reference. Aculeacin may be prepared using the procedure detailed in Mizuno et al., U.S. Pat. No. 3,978,210 which is herein incorporated by reference. The cyclic peptide of formula IIB where R' is —CH$_2$C(O)NH$_2$, R" is methyl, R"' is hydrogen, R$^{x1}$, R$^{x2}$, R$^{y1}$, R$^{y3}$, R$^{y4}$ are hydroxy may be prepared using the procedure detailed in U.S. Pat. No. 5,021,341, which is herein incorporated by reference.

The dideoxy compounds of formula IIB are prepared by removing the benzylic and aminal hydroxy groups (R$^{x2}$ and R$^{x1}$, respectively). The hydroxy groups may be removed by subjecting a non-dideoxy compound of formula IIB (where R$_2$ is hydrogen or acyl) to a strong acid and a reducing agent at a temperature of between −50° C. and 70° C., in a suitable solvent. Typical strong acids include trichloroacetic acid, trifluoroacetic acid or boron trifluoride etherate. A preferred strong acid is trifluoroacetic acid. Typical reducing agents include sodium cyanoborohydride or triethylsilane. A preferred reducing agent is triethylsilane. Suitable solvents include CH$_2$Cl$_2$, chloroform or acetic acid, preferably CH$_2$Cl$_2$. The strong acid is present in an amount of from 2 to 60 mol per mol of substrate, and the reducing agent is present in an amount of 2 to 60 mol per mol of substrate. This process affords selective removal of the aminal and benzylic hydroxy groups.

The semi-synthetic cyclic peptides of formula IIB may be prepared by deacylating the naturally occurring cyclic peptides using procedures known in the art to provide the corresponding amino nucleus (compound of formula IIB where R$_2$ is hydrogen). This reaction is typically carried out enzymatically, by exposing the naturally occurring cyclic peptide to a deacylase enzyme. The deacylase enzyme may be obtained from the microorganism *Actinoplanes utahensis* and used substantially as described in U.S. Pat. Nos. 4,293, 482 and 4,304,716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally-occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), FR901379 (palmitoyl side chain) and the like. A preferred naturally-occurring cyclic peptide is echinocandin B (compound of formula IIB where R', R", and R'" are each methyl, $R^{x1}$, $R^{x2}$, $R^{y1}$, $R^{y2}$, $R^{y3}$, $R^{y4}$ are each hydroxy, and $R_2$ is linoleoyl).

The amino nucleus is then re-acylated using procedures known in the art to provide a compound of formula II where $R_2$ is a semi-synthetic acyl group. For example, the amino nucleus may be acylated by reaction with an appropriately substituted acyl halide, preferably in she presence of an acid scavenger such as a tertiary amine, such as $Et_3N$. The reaction is typically carried out at a temperature of from about −20° C. to about 25° C. Typical solvents for this reaction include polar aprotic solvents such as dioxane or DMF. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include DCC, N,N'-carbonyldiimidazole, BOP-CL, EEDQ, PyBOP and the like.

In addition, the amino nucleus may be acylated with an activated ester of a carboxylic acid (RCOOH) such as an ester of a carboxylic acid of the formula $R_2$-COOH and p-nitrophenyl, 2,4,5-trichlorophenyl, hydroxybenzotriazole hydrate ($HOBT.H_2O$), pentafluorophenol, N-hydroxysuccinimide and the like. Preferred acylating moieties are the active esters of the carboxylic acid $R_2$—COOH such as 2,4,5-trichlorophenyl ester and HOBT ester. The reaction is typically carried out for about 1–65 hours at a temperature from about 0° C. to about 30° C. in an aprotic solvent. The reaction is generally complete after about 24–48 hours when carried out a temperature of from about 15° C. to about 30° C. Typical solvents for this reaction are THF and DMF or a mixture of such solvents. The amino nucleus is generally employed in equimolar proportions or with a slight excess of the amino nucleus relative to the activated ester.

The cyclic peptides are phosphonylated by reaction with the pyrophosphonate in the presence of a base. Typical bases include LiOH, sodium hydride, $Et_3N$, NMM, lithium trimethylsilanolate (LiOTMS), lithium t-butoxide (t-BuOLi), lithium bis(trimethylsilyl)amide (LHMDS), pyridine and the like. A preferred base is LiOtBu. The reaction is typically carried out for about 15 minutes to about 6 h at a temperature of from about −30° C. to about 40° C. in a suitable solvent. Suitable solvents include THF, DMF, dimethylacetamide, 1,2-dimethoxyethane, dimethylsulfoxide (DMSO) and the like. The reaction is generally complete in about 30 minutes to about 3 h when carried out under these conditions. The pyrophosphonate reactant is generally employed in equimolar proportions to about a one mol excess relative to the cyclic peptide in the presence of an equimolar or slight excess of the base. Phosphonylation of a cyclic peptide with unprotected aminal hydroxy groups ($R^{x1}$ and $R^{x2}$) is typically carried out at a temperature from about −30° C. to about −15° C. due to the sensitivity of the nucleus to the base whereas phosphonylation of a cyclic peptide with protected aminal hydroxy groups or a dideoxy cyclic peptide can be carried out at slightly higher temperatures.

The phosphonylated cyclic peptide is readily converted to the corresponding phosphonic acid derivative using conditions known in the art. For example, the phosphonate compounds may be catalytically hydrogenated by exposure to 1–3 atmospheres of hydrogen gas ($H_2$) in the presence of a catalyst such as palladium or platinum on a solid support and in the presence of a base such as $Et_3N$, NMM, pyridine, diisopropylethylamine or the like, in a suitable solvent such as THF, DMF or a THF/DMF mixture. A preferred base is $Et_3N$. A preferred catalyst is palladium-on-carbon (Pd/C). Solvent choice is not critical so long as the solvent employed is inert to the ongoing reaction and the reactant is sufficiently solubilized to effect the desired reaction. The reaction is generally substantially complete after about 1 to 24 hours when conducted at a temperature of from about 0° C. to about 40° C. The reaction is preferably conducted at a temperature of from about 20° C. to about 30° C. for about 2 to 5 hours. Alternatively, the phosphonylated cyclic peptide may be converted by chemical hydrogenation such as exposure to an alkali metal in liquid ammonia.

The aminal hydroxy groups on the cyclic peptide may be optionally protected with an hydroxy-protecting group using procedures known in the art. For example, the cyclic peptide is reacted with a suitable hydroxy-protecting group in the presence of a catalyst at a temperature in the range of from about 0° C. to about 40° C. for about 1 to 5 hours in a mutual inert solvent. The hydroxy-protecting group is generally employed in an amount ranging from about equimolar proportions to about a 100 molar excess relative to the cyclic peptide, preferably in a large molar excess. Suitable catalysts include strong acids such as p-toluenesulfonic acid, camphorsulfonic acid (CSA), hydrochloric acid (HCl), sulfuric acid, trifluoroacetic acid ($CF_3COOH$) and the like. Typical solvents suitable for use in this reaction include any organic solvent such as dioxane. Solvent choice is not critical so long as the solvent employed is inert to the ongoing reaction and/or the reactants are sufficiently solubilized to effect the desired reaction. The reaction is preferably conducted at a temperature in the range of from about 20° C. to about 30° C. for about 2 to 4 hours. It is not necessary to protect the dideoxy compounds of formula II. After phosphonylating the protected cyclic peptide, the hydroxy-protecting groups may be removed according to procedures known in the art. For example, the protecting groups can be removed by reaction with a Lewis acid in a mutual inert organic solvent such as $CH_2Cl_2$. Examples of Lewis acids include trimethylsilyl bromide, boron trifluoride etherate and the like. The reaction is typically carried out at a temperature of from about 0° C. to about 40° C., preferably from about 20° C. to about 30° C. A preferred Lewis acid is boron trifluoride etherate.

The $R_2$—COOH precursor acids are prepared by hydrolyzing a nitrile of the formula $R_2$—CN or an ester of the formula $R_2$—COO($C_1$–$C_4$ alkyl). The nitrile and ester intermediates may be prepared using procedures known in the art.

For example, the nitrile and ester intermediates where $R_2$ is an alkoxy aryl moiety may be prepared using Procedure A or Procedure B. described below.

Procedure A

One equivalent of an alkyl bromide, iodide, or p-toluenesulfonate is added to a mixture containing one equivalent of a base, such as potassium t-butoxide or potassium carbonate ($K_2CO_3$), and one equivalent of an hydroxy aryl compound in 200–300mL of acetonitrile ($CH_3CN$). The reaction mixture is refluxed for 6 h and then concentrated in vacuo to provide a residue which is dissolved in a $Et_2O$/2N NaOH mixture. The resulting layers are separated and the organic layer is dried over magnesium sulfate ($MgSO_4$), filtered and dried to provide the alkoxy aryl product.

Procedure B

Diethylazodicarboxylate (1 equiv.) is added dropwise to a mixture containing an hydroxy aryl compound (1 equiv.), an alkyl alcohol (1 equiv.) and triphenylphosphine (1 equiv.) in 200–300 mL of THF. After 17 h, the solvent is removed in vacuo to provide a residue which is dissolved in $Et_2O$. The resulting mixture is washed with a 2N NaOH solution, dried over $MgSO_4$, filtered and concentrated to provide a product which is then crystallized from a $Et_2O$/pentane mixture or, if the product contains a tertiary amine, the hydrochloride salt is formed and crystallized from a methanol (MeOH)/EtOAc mixture.

The nitrile and ester intermediates where $R_2$ is an alkynyl or alkenyl aryl moiety may be prepared using Procedure C, below.

Procedure C

A mixture containing $Et_2O$ (2 equiv.), palladium dichloride (0.05 equiv.), triphenylphosphine (0.1 equiv.), cuprous iodide (0.025 equiv.) and an alkyne (1 equiv.) or an alkene (2 equiv.) is added to one equivalent of an aryl bromide, iodide, or trifluoromethanesulfonate in $CH_3CN$ (600 mL/0.1 mol of aryl reactant), under nitrogen ($N_2$). The resulting mixture is refluxed for 17 h and then the solvent is removed in vacuo to provide a residue which is slurried in 300 mL of $Et_2O$ and then filtered. The filtrate is washed with a 1N HCl solution, dried over $MgSO_4$, filtered and then dried to provide the product.

The ester intermediates where $R_2$ is a terphenyl moiety may be prepared using Procedure D, below.

Procedure D

1. Formation of Boronic Acid Reactant

Butyl lithium (1.2 equivalents) is added to one equivalent of a cold (−78° C.) aryl halide in THF. After 15 minutes, triisopropyl borate (2 equiv.) is added. After 10 minutes, the reaction mixture is warmed to room temperature and quenched by the addition of water ($H_2O$), followed by the addition of 1N HCl. The resulting layers are separated and the organic layer is concentrated in vacuo to provide a solid which is collected by filtration and washed with hexane.

2. Formation of Terphenyl Ester

Tetrakis(triphenylphosphine)palladium (0.03 equiv.) is added to a mixture containing an aryl boronic acid (1 equiv.), $K_2CO_3$ (1.5 equiv.) and methyl 4-iodobenzoate (1 equiv.) (or trichlorophenyl ester of iodobenzoate) in $N_2$-purged toluene. The reaction mixture is refluxed for 7 h and then decanted to remove the $K_2CO_3$ and dried in vacuo to provide a residue. This residue is triturated in $CH_3CN$ and filtered to provide the product.

The aryl nitrites and esters described above may be converted to the corresponding carboxylic acids by hydrolysis using Procedure E or Procedure F, below.

Procedure E

An aryl nitrile is dissolved in ethanol (EtOH) and an excess of 50% NaOH solution and refluxed for 2 h. Water is added to the reaction mixture until a solid precipitates. This solid is collected by filtration, added to a dioxane/6N HCl mixture and the resulting mixture is refluxed for 17 h. When the reaction is substantially complete, the carboxylic acid product is crystallized by the addition of $H_2O$ and then collected by filtration and dried in vacuo.

Procedure F

An excess of 2N NaOH is added to an aryl ester in MeOH, and the resulting solution is refluxed for 5 h and then acidified by the addition of excess HCl. Water is added to the reaction mixture until a solid (carboxylic acid) precipitates. The carboxylic acid is collected by filtration and dried in vacuo.

The carboxylic acids may be converted to the corresponding 2,4,5-trichlorophenyl esters using Procedure G, below. These activated esters are then used to acylate the amino nucleus, as described above in Reaction Scheme IC.

Procedure G

A mixture containing an aryl carboxylic acid (1 equiv.), 2,4,5-trichlorophenol (1 equiv.) and DCC (1 equiv.) in $CH_2Cl_2$ is stirred for 17 h and then filtered. The filtrate is concentrated to provide a residue which is dissolved in $Et_2O$, filtered, and then pentane is added until crystallization begins. The crystals are collected by filtration and dried in vacuo.

Alternatively, the carboxylic acid may be activated by conversion to the corresponding hydroxybenzotriazole ester using Procedure H, below.

Procedure H

An aryl carboxylic acid (1 equiv.) and a slight excess of N-mesylate substituted hydroxybenzotriazole (1.2 equiv.) were reacted in the presence of a slight excess of a base such as triethylamine ($Et_3N$) (1.3 equiv.) in DMF, under $N_2$. When the reaction was complete, the mixture was diluted with toluene and washed with $H_2O$. The organic portion was diluted with $H_2O$ and then filtered using t-butyl methyl ether (MTBE) for transferring the material. The resultant solid was washed with MTBE and then dried in vacuo.

The present invention may be used to phosphonylate any hydroxy groups, for example in alcohols and phenols. The phosphonylation agents described herein are particularly useful for phosphonylating hydroxy functions in compounds that have acid-sensitive functional groups. The alcohols may be obtained from commercial sources or prepared according to procedures known in the art.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

In addition, examples of the phosphonylation of various alcohols are provided to demonstrate the selective phosphonylation of an alcohol in a polyfunctional system and the ability to use the mild conditions with compounds having sensitive functionalities.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. The symbol "J" indicates the coupling constant in Hertz (Hz). Unless otherwise noted, NMR data refers to the free base of the subject compound. The NMR spectra were obtained on a General Electric QE-300 300 MHz instrument or a Bruker AC300 300 MHz instrument. The chemical shifts are expressed in delta (δ) values (parts per million downfield from tetramethylsilane).

Preparation 1

A. Di-(4-bromobenzyl) methylphosphonate

A cold (0° C.) solution of 4-bromobenzyl alcohol (22 g, 117.6 mmol) and 1H-tetrazole (0.34 g, 4.85 mmol) in $Et_2O$ (300 mL), was treated with diisopropylethylamine (24 mL, 137.8 mmol), followed by the dropwise addition of methylphosphonic dichloride (8.7 g, 65.45 mmol) (which was added while maintaining a temperature of 0–3.5° C.). After stirring at 0° C. for 30 minutes, the mixture was warmed to room temperature and allowed to react for an additional 4 h which resulted in the formation of a precipitate. The reaction was monitored using TLC (90:10 $CH_2Cl_2$/EtOAc). The precipitate was removed by suction filtration and then rinsed with $Et_2O$ (3×50 mL). The resultant filtrate was concentrated in vacuo and then redissolved in 10 mL of $CH_2Cl_2$, filtered through a sintered glass funnel of silica gel (68 g, packed with $CH_2Cl_2$) and then eluted using 95:5 $CH_2Cl_2$/EtOAc.

Yield: 22.7 g (89%)

TLC: $R_f$ 0.43 (9:1 $CH_2Cl_2$/EtOAc).

IR ($CHCl_3$): 3420, 3005, 1596, 1490, 1408 $cm^{-1}$.

$^1H$ NMR ($CDCl_3$): δ1.47 (d, 1H, J=17.65 Hz), 4.94 (m, 4H), 7.19 (d, 4H, J=8.29 Hz), 7.46 (d, 4H, J=8.31 Hz).

$^{13}C$ NMR (DMSO-$d_6$): δ9.63, 11.48, 65.35, 65.43, 121.21, 129.7, 131.27, 136.01, 136.09.

MS(FD$^+$): m/z 434.

Analysis for $C_{15}H_{15}BrO_3P$: Calcd: C, 41.51; H, 3.48; Br, 36.82; Found: C, 41.31; H, 3.34; Br, 37.21.

B. Sodium 4-bromobenzyl methylphosphonate

A mixture of Preparation 1A (17 g, 39.16 mmol) and NaI (11.7 g, 78.06 mmol) in anhydrous acetone (20 mL) was refluxed for 5 h, resulting in the formation of a precipitate. When the reaction was substantially complete, as indicated by TLC (90:10 $CH_2Cl_2$/EtOAc), the mixture was cooled to room temperature and suction filtered. The precipitate was slurried in acetone (20 mL) and then filtered to provide a yellow solid which was rinsed with acetone (4×30 mL) and then dried in vacuo.

Yield: 10 g of a white solid (88.9%).

IR ($CHCl_3$): 1489, 1307, 1281 $cm^{-1}$.

$^1H$ NMR ($D_2O$): δ1.29 (d, 3H, J=16.41 Hz), 4.87 (d, 2H, J=7.29 Hz), 7.36 (d, 2H, J=8.31 Hz), 7.59 (d, 2H, J=8.38 Hz).

MS (FAB$^+$): m/z 287.

Analysis for $C_8H_9BrNaO_3P$: Calcd: C, 33.48; H, 3.16; Found: C, 33.71; H, 3.11.

C. 4-Bromobenzyl methylphosphonic acid

A cold (0° C.) solution of Preparation 1B (7 g, 24.38 mmol) in THF (35 mL) was treated dropwise with 6M HCl (4.2 mL, 25.2 mmol). After removing the cooling bath, the mixture was stirred for 10 minutes resulting in the formation of a precipitate which was removed by filtration. The filtrate was concentrated in vacuo to provide a solid. This solid was redissolved in $CH_2Cl_2$ (75 mL), dried over sodium sulfate ($Na_2SO_4$), filtered and then dried in vacuo to provide 6.8 g of a white solid (96.3% UV pure using HPLC). This solid was redissolved in warm EtOAc (25 mL) and filtered through a fritted disc. The filtrate was concentrated in vacuo to half the volume and diluted with hexanes which resulted in the precipitation of a white powder. This powder was collected by filtration, washed with 80:20 hexanes/EtOAc and dried in vacuo.

Yield: 5.5 g.

HPLC showed 99% UV purity. Spectral data was consistent with the material prepared in Preparation 4.

Preparation 2

A. Dibenzyl methylphosphonate

The compound was prepared substantially in accordance with the procedure detailed in Preparation 1A.

TLC: $R_f$ 0.36 (9:1 $CH_2Cl_2$/EtOAc).

IR ($CHCl_3$): 3673, 3415, 3036, 1498, 1456, 1312, 1238 $cm^{-1}$.

$^1H$ NMR ($CDCl_3$): δ1.46 (d, 3H, J=17.65 Hz), 5.00 (m, 4H), 7.34 (s, 10H).

$^{13}C$ NMR (DMSO-$d_6$): δ9.74, 11.60, 66.17, 66.25, 127.69, 128.09, 128.40, 136.62, 136.70.

MS(FD$^+$): M$^+$=277.

B. Sodium benzyl methylphosphonate

The compound was prepared substantially in accordance with Preparation 1B using Preparation 2A, with the exception that the desired compound was extracted from the reaction mixture after acidification (due to contamination with the disodium salt).

$^1H$ NMR ($D_2O$): δ1.31 (d, 3H, J=16.35 Hz), 4.92 (d, 2H, J=7.08 Hz), 7.45 (m, 5H).

C. Benzyl methylphosphonic acid

A solution of Preparation 2B (400 mg containing 20–30% of the disodium salt) in $H_2O$ (0.5 mL) was adjusted to pH 3 by the addition of 1N HCl. The resultant mixture was extracted with EtOAc (3×5 mL) and the combined extracts were dried over $Na_2SO_4$, filtered and concentrated in vacuo to provide an oil which was dried in vacuo.

Yield: 149 mg.

TLC: $R_f$ 0.18 (8:2:3 $CH_2Cl_2$/MeOH/HOAc).

IR ($CHCl_3$): 3600–3000, 1456, 1314 $cm^{-1}$.

$^1H$ NMR ($CDCl_3$): δ1.49 (d, 3H, J=17.88 Hz), 5.03 (d, 2H, J=7.88 Hz), 7.36 (m, 5H), 12.61 (br.s, 1H).

$^{13}C$ NMR (75 MHz, $CDCl_3$): δ10.85, 12.79, 66.58, 66.66, 127.80, 128.34, 128.58, 136.23, 136.32.

MS (FD$^+$): m/z 187 (MH$^+$).

Analysis for $C_8H_{11}O_3P$: Calcd: C, 51.62; H, 5.96; Found: C, 51.69; H, 5.89.

Preparation 3

A. Di-(4-methoxybenzyl) methylphosphonate

The compound was prepared substantially in accordance with Preparation 1A.

IR ($CHCl_3$): 3005, 2962, 1614, 1587, 1465, 1312, 1305, 1251, 1175, 1033, 1015 $cm^{-1}$.

$^1$H NMR (CDCl$_3$): δ1.41 (d, 3H, J=18 Hz), 3.79 (s, 3H), 4.88 (dd, 2H, J=12 Hz, 9 Hz), 4.97 (dd, 2H, J=12 Hz, 9 Hz), 6.88 (d, 2H, J=9 Hz), 7.29 (d, 2H, J=9 Hz).

$^{13}$C NMR(CDCl$_3$): δ159.76, 129.82, 128.55, 128.47, 113.95, 77.63, 77.20, 66.96, 66.88, 55.23, 12.75, 10.85.

MS (FD$^+$) M$^+$=336.

Analysis for C$_{17}$H$_{21}$O$_5$P: Calcd: C, 60.71; H, 6.29; Found: C, 60.99; H, 6.39.

B. Sodium 4-methoxybenzyl methylphosphonate

The compound was prepared substantially in accordance with Preparation 1B using Preparation 3A, with the exception that only 1.1 equivalents of NaI were used and the reaction was run at room temperature for 16 h.

Yield=70%.

1H NMR (D$_2$O): δ1.21 (d, 3H, J=18 Hz), 3.79 (s, 3H), 4.79 (d, 2H, J=8.7 Hz), 6.91 (d, 2H, J=9.6 Hz), 7.38 (d, 2H, J=9.6 Hz).

Analysis for C$_8$H$_{12}$O$_4$PNa: Calcd: C, 45.39; H, 5.08; Found: C, 46.01; H, 5.15.

Preparation 4

4-Bromobenzyl methylphosphonic Acid

A solution containing 4-bromobenzyl alcohol (49.4 g, 0.26 mol) and Et$_3$N (39 mL, 0.28 mol) in CH$_2$Cl$_2$ (150 mL) was slowly added to a cold (0° C.) solution of methyl phosphonic dichloride (36.96 g, 0.28 mol) in 200 mL of CH$_2$Cl$_2$, under N$_2$. When the reaction was substantially complete, as determined by HPLC, an additional 39 mL of Et$_3$N was added, followed by 20 mL of H$_2$O resulting in an exotherm up to 27° C., followed by an additional 30 mL of H$_2$O. According to HPLC, the reaction mixture contained 55% of the compound of Preparation 6, 4.5% of the desired compound and 20% of the compound of Preparation 1A. The reaction mixture was transferred to a separatory funnel and washed with 1N HCl (2×150 mL). The organic layer was combined with 150 mL of 2N NaOH and 50 mL of H$_2$O, stirred overnight to hydrolyze the compound of Preparation 6 to the desired compound and then separated. The aqueous layer was washed with CH$_2$Cl$_2$ (2×150 mL), acidified with 22 mL of 12N HCl and then extracted with CH$_2$Cl$_2$ (400 mL). The organic extract was dried over Na$_2$SO$_4$, filtered and then dried in vacuo to provide 53.74 g of a white solid which was suspended in EtOAc (110 mL), stirred vigorously for 3 h, isolated by filtration and then dried in vacuo (at 50° C.).

Yield: 48.72 g (71% yield).

IR (CHCl$_3$): 3600–3000, 1597, 1490, 1314 cm$^{-1}$.

$^1$H NMR (CDCl$_3$): δ1.50 (d, 3H, J=18 Hz), 4.97 (d, 2H, J=8 Hz), 7.23 (d, 2H, J=8 Hz), 7.48 (d, 2H, J=8 Hz), 12.41 (br.s, 1H).

$^{13}$C NMR (CDCl$_3$): δ10.81, 12.75, 65.75, 65.83, 122.39, 129.36, 131.74, 135.20, 135.29.

Analysis for C$_8$H$_{10}$BrO$_3$P: Calcd: C, 36.25; H, 3.80; Found: C, 36.55; H, 3.86.

Preparation 5

Benzyl methylphosphonic Acid

The compound was prepared substantially as described in Preparation 4, using benzyl alcohol.

Yield: 88%.

Preparation 6

A. Syn/anti mixture of diastereomeric di-(4-bromobenzyl) dimethylpyrophosphanate A mixture containing Preparation 4 (70 g, 261.1 mmol) and DCC (24.7 g, 132.8 mmol) in EtOAc (700 mL) and CH$_2$Cl$_2$ (140 mL) was stirred for 1 h and then filtered. The filtrate was dried in vacuo to provide a solid which was suspended in heptane (340 mL) and stirred for 20 minutes, filtered and then dried in vacuo to provide a white solid.

Yield: 64.2 g (95% yield).

IR (CHCl$_3$): 3012, 1596, 1491, 1317, 1261 cm$^{-1}$.

$^1$H NMR(CDCl$_3$): δ1.65 and 1.70 (d, 3H, J=18 Hz); 5.21–5.01 (m, 2H), 7.23 and 7.26 (d, 2H, J=8 Hz), 7.48 and 7.49 (d, 2H, J=8 Hz).

$^{13}$C NMR (CDCl$_3$): δ12.00, 12.05, 12.09, 13.99, 14.04, 14.09, 67.05, 67.10, 67.15, 67.19, 122.80, 129.72, 129.80, 131.86, 134.61.

MS (FD$^+$): m/z 508, 509, 510, 511, 512, 513, 514, 515 for $^{79}$Br and $^{81}$Br combinations.

Analysis for C$_{16}$H$_{18}$Br$_2$O$_5$P$_2$: Calcd: C, 37.53; H. 3.54; Found: C, 37.74; H. 3.59.

B. Syn or anti diastereomer

The mixture of diastereomers isolated in Preparation 6A was separated by recrystallization. First, the product from Preparation 6A (820 mg) was dissolved in warm EtOAc (100 mL) and filtered. The filtrate was diluted with hexanes (100 mL) and allowed to stand at 4° C. for 4 days resulting in the formation of a white precipitate which was collected by filtration and rinsed three times with 80:20 hexanes/EtOAc (3×10 mL). The pure diastereomer thus obtained was not assigned unequivocally as the syn or anti diastereomer.

Yield: 570 mg.

$^1$H NMR (CDCl$_3$): δ1.67 (d, 6H, J=17.69 Hz), 5.09 (m,4H), 7.22 (d, 4H, J=8.46 Hz), 7.48 (d, 4H, J=8.31 Hz).

Preparation 7

Syn/anti-dibenzyl dimethylpyrophosphonate

To a solution of 7.37 g (39.6 mmol) of Preparation 5 in 50 mL of EtOAc, was added 4.1 g (19.8 mmol) of DCC. The resulting slurry was stirred for 30 minutes and filtered. The filtrate was evaporated to provide 7.0 g of an oil. Analysis by HPLC showed 96.3 area % product and 0.8 area % starting material. The material was used without further purification.

$^1$H NMR(CDCl$_3$): δ1.55–1.75 (m, 6H), 5.05–5.25 (m, 4H), 7.38 (m, 10 H)

MS(FD$^+$): m/z 355.

Preparation 8

A. 4-Bromo-4'-pentyloxybiphenyl

Anhydrous K$_2$CO$_3$ (416 g, 3 mol) was added to a mixture of 4-bromo-4'-hydroxybiphenyl (300 g, 1.2 mol), 1-iodopentane (234 mL, 1.79 mol) and 2-butanone (600 mL). The reaction mixture was refluxed for 44 h until TLC (85:15 hexanes/EtOAc) showed complete consumption of the bromo alcohol. The mixture was cooled to about 30° C., diluted with CH$_2$Cl$_2$ (600 mL) and then filtered. The filtrate was washed twice with H$_2$O and twice with a saturated aqueous NaCl solution, dried over anhydrous Na$_2$SO$_4$, filtered and then dried at reduced pressure to provide a solid. This solid was isolated by filtration, washed repeatedly with a total of 2 L of ice-cold heptane to remove all traces of iodopentane and then dried overnight under high vacuum.

Yield: 340 g (88%) of a white powder.

Alternative Preparation of 4-bromo-4'-pentyloxybiphenyl

4-Bromo-4'-hydroxybiphenyl (12.5 g, 50.2 mmol) was added to a solution of NaOH (2.28 g, 97% pure, 55.2 mmol)

in deionized H₂O (150 mL), followed by the addition of 1-iodopentane (11.9 g, 60.2 mmol) and tetrabutylammonium bromide (0.82 g, 2.51 mmol). The mixture was stirred at 90° C. for 3.75 h until the solids went into solution. Then, as the reaction proceeded, the desired product began to precipitate. The mixture was slowly cooled and then filtered to provide a solid which was washed with deionized water until the pH of the filtrate was neutral and then dried for 16 h in a vacuum oven at 30° C.

Yield: 15.41 g (96%) of 5a. $R_f$ 0.5 (97:3 hexanes/EtOAc).
¹H NMR: δ0.93 (t, 3H, J=6.9 Hz); 1.41 (m, 4H); 1.79 (m, 2H); 3.97 (t, 2H, J=6.6 Hz); 6.98 (m, 2H); 7.23 (m, 6H).
¹³C NMR: δ14.03; 22.43; 28.22; 28.98; 68.12; 114.91; 120.71; 127.93; 128.27; 131.77; 132.24; 139.82; 159.03.
MS (FAB⁺): m/z 320.
IR(CHCl₃): 2960, 2936, 2874, 1608, 1518, 1485, 1475 cm⁻¹.
Analysis for C₁₇H₁₉BrO: Calcd: C, 63.96; H. 6.00; Br, 25.0; Found: C, 64.10; H. 5.97; Br, 25.28.

B. 4-Boronic Acid-4'-pentyloxybiphenyl

To a cold (−20° C.) mixture of Preparation 8A (100 g, 0.31 mol) in MTBE (1 L), was slowly added n-butyl lithium (150 mL of a 2.5M hexanes solution, 0.37 mol) dropwise under N₂, while maintaining the internal temperature between −19° and −18° C. The resultant mixture was stirred for 3.5 h between −17° and −16° C. which resulted in light yellow-green solution. This solution was cooled to −78° C. and diluted with 100 mL of anhydrous THF which resulted in a white precipitate. Then, a cold (−78° C.) solution of triisopropylborate (145 mL, 0.62 mol) in MTBE (200 mL), under nitrogen was added dropwise over 1.5 h while maintaining the reaction temperature between −78° and −74° C. The resultant reaction mixture was stirred for 1.5 h at −78° C., then allowed to warm to −50° C. over 1 h at which time the cooling bath was removed and the mixture was stirred overnight (16–21 h) which resulted in a white precipitate. The mixture was shaken vigorously with 2M HCl (1000 mL) for 5 minutes and then the resulting layers were separated and the organic layer was dried at reduced pressure to provide a residue. This residue was diluted with MTBE (100 mL), followed by heptane (800 mL) to provide a white powder which isolated by suction filtration and washed 3 times with heptane (300 mL).

Yield: 88 g (98%).
$R_f$ 0.45 (95:5 CH₂Cl₂/MeOH).
¹H NMR: δ0.92 (m, 3H); 1.41 (m, 4H); 1.80 (m, 2H); 4.00 (m, 2H); 6.99 (m, 2H); 7.45–7.63 (m, 3H); 7.67 (m, 2H); 8.24 (d, 1H, J=8.3 Hz).
¹³C NMR: 14.01; 22.26; 28.03; 28.77; 39.61; 39.89; 40.17; 40.45; 67.82; 114.77; 125.32; 127.83; 132.93; 134.84; 141.88; 158.71.
MS(FD⁺): m/z 284.
IR(CHCl₃): 2959, 2952, 2874, 1606, 1526, 1500 cm⁻¹.

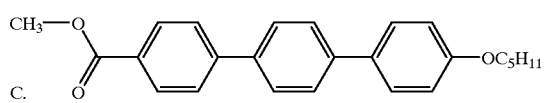

C.

A solution of toluene (174 mL) and propanol (20 mL) was degassed 3 times by applying vacuum to the solution for 20–30 seconds followed by purging with N₂. A 2M solution of Na₂CO₃ was also degassed. The toluene/propanol solution (97 mL) was added to a mixture of methyl 4-iodobenzoate (14.12 g, 53.9 mmol) and Preparation 8B (15.0 g, 52.8 mmol), followed by a degassed 2M aqueous Na₂CO₃ solution (29 mL, 58.0 mmol). The resultant mixture was degassed 2 times for 20–30 seconds each under a positive pressure of N₂, followed by the addition of palladium (II) acetate (0.24 g, 1.1 mmol) and triphenylphosphine (0.84 g, 3.2 mmol) and then degassed 2 more times. The reaction mixture was then refluxed under N₂ for 5 h resulting in a light-yellow mixture. This mixture was cooled to 23° C. resulting in the formation of a precipitate which was collected by filtration, washed successively with toluene (123 mL), 2:1 MTBE/EtOAc (143 mL), deionized water (123 mL) and 2:1 NTBE/EtOAc (42 mL) and then dried for 16 h in a vacuum oven at 35° C.

Yield: 18.7 g (94%).
$R_f$ 0.48 (benzene).
¹H NMR: δ0.93 (t, 3H, J=6.80 Hz); 1.42 (m, 4H); 1.81 (m, 2H); 3.95 (s, 3H); 4.00 (t, 2H, J=6.48 Hz); 6.97 (d, 2H, J=8.52 Hz); 7.55 (d, 2H, J=8.52 Hz); 7.66 (m, 6H), 8.10 (d, 2H, J=8.20 Hz).
MS(FD): m/z 374.
IR(KBr): 2938, 1723 cm⁻¹.
Analysis for C₂₅H₂₆O₃: Calcd: C, 80.18; H. 7.00; Found: C, 79.91; H. 6.94.

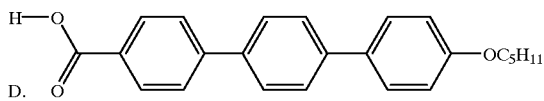

D.

A mixture of Preparation 8C (80 g, 0.21 mol), 5M KOH (160 mL) and cetyltrimethylammonium bromide (4.8 g, 0.013 mol) in xylene (800 mL) was refluxed for 3 h and then cooled to 10° C. and filtered to provide a white solid. This solid was washed 3 times with H₂O (500 mL each) to remove the catalyst and most of the base. The resultant material was treated with DME (500 ml). The pH of the solution was adjusted to pH by the addition of 6M HCl (100 mL). The resultant mixture was refluxed for 30 minutes while periodically checking the pH to assure that it remained acidic, then cooled and filtered. The resulting solid was washed successively with MTBE (400 mL) and water (4×400 mL) until the washings were neutral to litmus.

Yield: 76 g (98% yield).
¹H NMR δ0.89 (t, 3H, J=6.82 Hz), 1.38 (m, 4H), 1.73 (m, 2H), 3.96 (t, 2H, J=6.3 Hz), 6.95 (d, 2H, J=8.56 Hz), 7.57 (d, 2H, J=8.54 Hz), 7.64–7.74 (m, 6H), 8.00 (d, 2H, J=8.21 Hz), 8.09 (s, 1H).
MS(FD⁺) m/z 360.
IR(KBr): 2958, 2937, 2872, 1688 cm⁻¹.
Analysis for C₂₄H₂₄O₃: Calcd: C, 79.97; H. 6.71; Found: C, 80.50; H. 6.77.

E. HOBT ester of Preparation 8D

1. Formation of HOBT mesylate

To a cold (0° C.) mixture of hydroxybenzotriazole hydrate (200 g, 1.48 mol) in anhydrous CH₂Cl₂ (1.5 L), was slowly added anhydrous Et₃N (268 mL, 1.92 mol) while maintaining a temperature of 0–10° C., followed by the addition of methanesulfonyl chloride (126 mL, 1.63 mol) while maintaining a temperature of 0–5° C. The resultant mixture was stirred for 3 h at 0° C. and washed successively with cold water (2×1.2 L) and brine (1.2 L). The combined organic extracts were concentrated at reduced pressure to provide a solid. This solid was recrystallized from CH$_2$Cl$_2$ (100 mL) and heptane (1 L). The crystals were collected by suction filtration and washed repeatedly with a total of 1. L of heptane and then dried overnight under high vacuum (0.5 mm Hg).

Yield: 245 g (78%)

R$_f$ 0.55 (1:1 hexanes/CH$_2$Cl$_2$)

$^1$H NMR: δ3.58 (s, 3H), 7.46 (t, 1H, J=7.60 Hz), 7.60 (d, 1H, J=8.28 Hz), 7.65 (d, 1H, J=8.56 Hz), 7.68 (d, 1H, J=8.20 Hz), 8.05 (d, 1H, J=8.41 Hz).

2. Formation of HOBT ester

A mixture of Preparation 8D (50 g, 0.14 mol) and Preparation 8E-1 (36 g, 0.17 mol) in DMF (650 mL) was treated dropwise with Et$_3$N (25 mL, 0.18 mol), under N$_2$. The resultant mixture was stirred for 4 h at room temperature until all the acid was consumed, as determined by TLC (95:5 CH$_2$Cl$_2$/MeOH).

When all the acid was consumed, an aliquot of the reaction mixture (~3 pipet drops) gave a clear homogeneous solution when diluted with 3 mL of 1:1 CH$_2$Cl$_2$/THF. The reaction mixture was then diluted with toluene (500 mL), washed with water (500 mL). The organic layer (containing solid product) was diluted with water (500 mL) and filtered using MTBE for transferring. The solid was rinsed with MTBE (2×400 mL) and dried under vacuum to provide green-white flakes of material. NOTE: This material could be dissolved in THF and filtered to remove any remaining metal contamination.

Yield: 61 g (92%).

R$_f$ 0.68 (1:1 CH$_2$Cl$_2$/hexanes).

$^1$H NMR: δ0.93 (t, 3H, J=7.0 Hz), 1.42 (m, 4H), 1.81 (m, 2H), 4.00 (t, 2H, J=6.53 Hz), 6.99 (d, 2H, J=8.6 Hz), 7.42–7.59 (m, 5H), 7.71 (dd, 4H, J=13.91 Hz, 8.40 Hz), 7.86 (d, 2H, J=8.30 Hz), 8.11 (d, 1H, J=8.31 Hz), 8.35 (d, 2H, J=8.33 Hz)

$^{13}$C NMR: δ14.03, 22.44, 28.18, 28.94, 40.10, 40.37, 68.11, 108.45, 110.11, 114.95, 118.71, 120.48, 123.04, 124.94, 124.99, 127.00, 127.23, 127.51, 127.73, 128.06, 128.82, 128.86, 131.35, 132.30, 137.15, 141.43, 143.54, 147.85, 159.15, 162.73.

MS(FD$^+$): m/z 477.

IR(CHCl$_3$): 2960, 2936, 2874, 1783, 1606 cm$^{-1}$.

Analysis for C$_{30}$H$_{27}$N$_3$O$_3$: Calcd: C, 75.45; H, 5.70; N, 8.80; Found: C, 75.69; H, 5.58; N, 8.92.

Preparation 9

A. Cyclic peptide of formula IIB where R', R", and R'" are each methyl, R$^{x1}$, R$^{x2}$, R$^{y1}$, R$^{y2}$, R$^{y3}$, R$^{y4}$ are each hydroxy

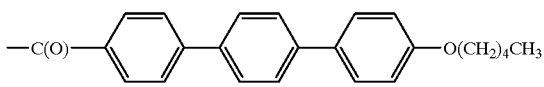

NOTE: Deionized water was used throughout this operation. A mixture of Preparation 8E (11 g, 23 mmol) and the cyclic peptide of formula IIB where R', R", and R'" are methyl, R$^{x1}$, R$^{x2}$, R$^{y1}$, R$^{y2}$, R$^{y3}$, R$^{y4}$ are each hydroxy and R$_2$ is hydrogen (92% pure by HPLC, 19.25 g, 22.2 mmol) in anhydrous DMF (275 mL) was stirred, under N$_2$ for 4 h (until HPLC showed complete consumption of the cyclic peptide starting material). The mixture was filtered through a bed of celite and the filtrate was concentrated under reduced pressure at 35° C. to provide a paste that could be stirred. This paste was poured into MTBE (500 mL) which resulted in the precipitation of a fine powder which was collected by vacuum filtration and dried to provide 27 g of crude material. This material was crushed to a powder with a mortar and pestle, slurried for 5 minutes in toluene (200 mL), suction filtered (slow filtered), rinsed with MTBE (100 mL) and then dried in vacuo to provide a yellow solid.

Yield: 23 g (95% pure by HPLC, retention time=7.79 min).

Alternatively, Preparation 9A may be carried out using an excess of the cyclic nucleus (1.1 equiv.). When the reaction was substantially complete, as indicated by HPLC, the crude material (10 g of a powder) was added portion-wise to a vigorously stirred mixture of 9:1 acetone/water (60mL). Celite (2.5 g, pre-washed with a 9:1 acetone/water mixture) was added to the resultant suspension. After stirring for 2 minutes, the mixture was filtered through a bed of celite (prewashed with 9:1 acetone/water) and the cake was rinsed twice with 9:1 acetone/water (10 mL). The filtrate was poured into a beaker of deionized water (200 mL) while gently swirling the mixture which resulted in the formation of a precipitate. This precipitate was collected by suction filtration, rinsed with H$_2$O (4×25 mL), and then dried in vacuo at room temperature.

Yield: 6.81 g (97% pure by HPLC).

The product was further purified using preparatory HPLC chromatography.

R$_f$ 0.29 (80:20 CHCl$_3$/MeOH).

HRMS (FAB$^+$): m/z for C$_{58}$H$_{74}$N$_7$O$_7$ Calcd: 1140.5141; Found: 1140.5103.

IR(KBr): 3365, 2934, 1632, 1518 cm$^{-1}$.

B. Cyclic peptide of formula I where R', R", and R'" are each methyl, R$^{x1}$ and R$^{x2}$ are each hydrogen, R$^{y1}$, R$^{y2}$, R$^{y3}$, R$^{y4}$ are each hydroxy and R$_2$ is

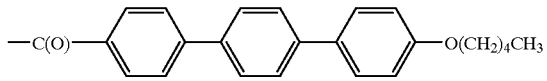

To a cool (16° C.) solution containing Preparation 9A (0.235 kg, 0.207 mol, 1.0 equiv.) and triethylsilane (0.78 kg, 6.70 mol, 30 equiv.) in CH$_2$C$_{12}$ (0.77 L), was slowly added CF$_3$COOH (0.978 kg, 8.56 mol, 35 equiv.) while maintaining the temperature at 20° C. After 90 minutes, the mixture was cooled to −5° C., diluted with THF (4.0 L) and poured into a solution of K$_2$CO$_3$ (0.862 kg, 8.62 mol, 38.5 equiv.) in H$_2$O (4.0 L). The resulting layers were separated and the organic layer was dried in vacuo to provide 0.308 kg of crude material (yield: 83.1% after correction for potency (61.7%)). The crude material was purified using HPLC (HP20SS column by step gradient elution; solvent A—42:58 MeCN/0.1% HOAc at pH 5; solvent B—60:40 MeCN/0.1% HOAc at pH 5).

IR (CHCl$_3$): 3366, 2934, 1636, 1517 cm$^{-1}$.

HRMS (FAB$^+$) m/z for C$_{58}$H$_{74}$N$_7$O$_{15}$: Calcd: 1108.5243; Found: 1108.5265.

Analysis for C$_{58}$H$_{73}$N$_7$O$_{15}$: Calcd: C, 62.85; H, 6.63; N, 8.85; Found: C, 62.90; H, 6.49; N, 8.96.

Preparation 10

A. Methyl-6-O-t-butyldimethylsilyl-α-D-mannopyranoside

The C-6 hydroxy of methyl-α-D-mannopyrannoside (7.20 g, 37.1 mmol) was protected as the t-butyldimethylsilyl ether using imidazole (5.05 g, 74.2 mmol) and t-butyldimethylsilyl chloride (6.15 g, 40.8 mmol) in DMF (50 mL). The crude product was purified using silica gel chromatography (2:1 EtOAc:hexanes).

Yield: 7.00 g (61%) of a white solid.

B. Methyl-6-O-t-butyldimethylsilyl-2,3-O-isopropylidene-α-D-mannopyranoside

To a solution containing Preparation 10A (3.3 g, 10.72 mmol) and pyridinium p-toluenesulfonate (2 g, 7.5 mmol) in acetone (20 mL), was added 2,2-dimethoxypropane (13.2 mL, 107.2 mmol). The reaction mixture was stirred for 1 h at room temperature. When the reaction was substantially complete, as indicated by TLC, the reaction was quenched by the addition of a saturated aqueous sodium bicarbonate solution (NaHCO$_3$) (30 mL) and then diluted with EtOAc. The resulting layers were separated and the aqueous layer was extracted with EtOAc (2×30 mL). The combined organic extracts were washed with brine (50 mL), dried over Na$_2$SO$_4$, filtered and then concentrated in vacuo to provide a viscous yellow oil. This oil was purified using silica gel chromatography (1:1 hexanes/Et$_2$O).

Yield: 3.4 g (91%) of a clear viscous oil.

IR (CHCl$_3$): 3590 cm$^{-1}$ (OH).

$^1$H NMR (DMSO-d$_6$): δ0.02 (s, 6H), 0.84 (s, 9H), 1.22 (s, 3H), 1.36 (s, 3H), 3.28 (s, 3H), 3.28–3.32 (m, 1H), 3.56–3.62 (dd, 1H, J=3, 1 Hz), 3.80–3.92 (m, 2H), 3.96 (d, 1H, J=3 Hz), 4.78 (s, 1H), 5.16 (d, 1H, J=3 Hz);.

$^{13}$C NMR (DMSO-d$_6$): 18.35, 26.15, 26.66, 28.36, 54.12, 59.57, 62.92, 68.28, 71.36, 75.51, 79.07, 07.58, 108.61.

MS (FD+): m/z 349.

Analysis for C$_{16}$H$_{32}$O$_6$Si: Calcd: C, 55.14; H, 9.25; Found: C, 54.91; H, 9.14.

Preparation 11

Methyl-6-O-t-butyldiphenylsilyl-2,3-O-isopropylidene-α-D-mannopyranoside

In a similar manner to Preparation 10, the C-6 hydroxy of methyl-α-D-mannopyrannoside was protected as the t-butyldiphenylsilyl ether, followed by formation of the dimethyl acetal to provide a clear oil.

IR (CHCl$_3$): 3595 cm$^{-1}$ (OH).

$^1$H NMR (DMSO-d$_6$): δ1.02 (s, 9H), 1.28 (s, 3H), 1.42 (s, 3H), 3.38 (s, 3H), 3.38–3.44 (m, 1H), 3.48–3.54 (m, 1H), 3.72–3.80 (dd, 1H, J=3, 1 Hz), 3.92–4.00 (m, 2H), 4.06–4.12 (d, 1H, J=3 Hz), 4.92 (s, 1H), 5.22 (d, 1H, J=3 Hz), 7.36–7.50 (m, 6H), 7.66–7.80 (m, 4H).

$^{13}$C NMR (DMSO-d$_6$): δ19.6, 27.31, 28.72, 54.57, 64.17, 68.64, 71.67, 75.91, 79.37, 98.07, 109.04, 128.59, 130.56, 133.94, 135.78, 136.03.

MS (FD+): m/z 473.

Analysis for C$_{26}$H$_{36}$O$_6$Si: Calcd: C, 66.07; H, 7.68; Found: C, 65.98; H, 7.50.

Preparation 12

A. Methyl-4,6-O-benzylidene-α-D-glucopyranoside

To a mixture of methyl-α-D-glucopyrannoside (10.05 g, 51.2 mmol) and camphor sulfonic acid (0.985 g, 4.24 mmol) in CH$_3$CN (70 mL), was slowly added benzaldehyde dimethylacetal (9.28 mL, 61.0 mmol). The resulting mixture was reacted overnight at reflux temperature, under N$_2$. When the reaction was substantially complete, as indicated by TLC (90:10 CH$_2$Cl$_2$/MeOH), an excess of Et$_3$N (10 mL, 71 mmol) was added and the resulting mixture was concentrated in vacuo to provide a tan solid. This solid was recrystallized from warm propanol/pyridine (28 mL/0.5 mL), collected by vacuum filtration, rinsed with 1:1 MTBE/hexanes (50 mL) and then dried in vacuo.

Yield: 9.08 g (62%) of a yellow-white solid.

IR (CHCl$_3$): 3595 cm$^{-1}$ (OH).

$^1$H NMR (DMSO-d$_6$): δ3.36 (s, 3H), 3.36–3.42 (m, 1H), 3.54–3.62 (m, 1H), 3.64–3.74 (t, 1H, J=6 Hz), 4.16–4.22 (dd, 1H, J=3, 1 Hz), 4.64 (d, 1H, J=2 Hz), 5.00 (d, 1H, J=3 Hz), 5.18 (d, 1H, J=3 Hz), 5.58 (s, 1H), 7.36–7.52 (m, 5H).

$^{13}$C NMR (DMSO-d$_6$): δ26.62, 55.75, 63.38, 69.18, 70.89, 73.42, 82.35, 101.55, 101.86, 127.39, 129.01, 129.83, 138.83.

MS (FD+): m/z 282.

B. Methyl-2,3-di-O-acetyl-4,6-O-benzylidene-α-D-glucopyranoside

Acetic anhydride (2.1 mL, 22.16 mmol) was slowly added to a solution of Preparation 12A (2.844 g, 10.07 mmol), Et$_3$N (3.5 mL, 25.2 mmol) and a catalytic amount of 4-dimethylaminopyridine (DMAP) (0.10 g) in CH$_2$Cl$_2$ (25 mL). When the reaction was substantially complete, as indicated by TLC (1:1 hexanes/EtOAc), the mixture was diluted with CH$_2$Cl$_2$ (25 mL) and aqueous NaHCO$_3$ (25 mL). The resulting layers were separated and the aqueous layer extracted with CH$_2$Cl$_2$ (2×30 mL). The combined organic extracts were washed with brine (50 mL), dried over Na$_2$SO$_4$, filtered and then concentrated in vacuo to provide a clear viscous oil which solidified on standing. This material was used without further purification.

Yield: 3.35 g (91%).

$^1$H NMR(CDCl$_3$): δ2.02 (S, 3H), 2.06 (s, 3H), 3.46 (s, 3H), 3.62–3.66 (t, 1H, J=4.5 Hz), 3.70–3.76 (t, 1H, J=4.5 Hz), 3.92–3.98 (m, 1H), 4.36 (q, 1H, J=2 Hz), 4.98 (m, 2H), 5.50 (s, 1H), 5.58 (t, 1H, J=3 Hz), 7.32–7.50 (m, 5H).

C. Methyl-2,3-di-O-acetyl-6-O-benzyl-α-D-glucopyranoside

To a cold (0° C.) solution of Preparation 12B (3.35 g, 9.14 mmol) in CH$_2$Cl$_2$ (25 mL), was slowly added CF$_3$COOH (3.52 mL, 45.7 mmol). After stirring for 5 minutes, triethylsilane (7.30 mL, 45.7 mmol) was slowly added. The reaction mixture was then allowed to warm to room temperature. When the reaction was substantially complete, as indicated by TLC (1:1 hexanes/EtOAc), the mixture was diluted with EtOAc (50 mL) and aqueous NaHCO$_3$ (60 mL). The resulting layers were separated and the aqueous layer extracted with CH$_2$Cl$_2$ (2×50 mL). The combined organic extracts were washed with brine (60 mL), dried over Na$_2$SO$_4$, filtered and then concentrated in vacuo to provide a yellow oil. The oil was purified using silica gel chromatography to provide a clear viscous oil.

Yield: 3.052 g (91%).

IR (CHCl$_3$): 3490 (OH), 1745 cm$^{-1}$ (C=O).

$^1$H NMR (DMSO-d$_6$): δ1.98 (s, 3H), 2.02 (s, 3H), 3.34 (s, 3H), 3.40–3.56 (m, 1H), 3.58–3.76 (m, 2H), 4.56 (s, 2H), 4.62–4.70 (dd, 1H, J=3, 1 Hz), 4.82 (d, 1H, J=1.5 Hz), 5.12–5.22 (dd, 1H, J=6, 1 Hz), 5.56 (d, 1H, J=3 Hz), 7.24–7.42 (m, 5H).

$^{13}$C MMR (DMSO-d$_6$): δ20.61, 20.88, 54.61, 67.89, 69.08, 70.82, 71.16, 72.36, 72.49, 96.29, 127.48, 128.38, 138.62, 169.88, 169.99.

MS (FD+): m/z 368.

Preparation 13

A. Methyl-2,3,6-tri-O-benzyl-4,6-O-benzylidene-α-D-glucopyranoside

A solution of Preparation 12A (1.88 g, 6.66 mmol) and tetrabutylammonium iodide (0.246 g, 0.67 mmol) in DMF (10 mL) was slowly added to a cold (0° C.) stirring mixture of sodium hydride (60% oil dispersion, washed with hexanes, 0.67 g, 16.6 mmol) in DMF (10 mL). The resulting mixture was cooled to 0° C., followed by the dropwise addition of benzyl bromide (1.75 mL, 14.6 mmol). After stirring at 0° C. for 10 minutes, the mixture was allowed to warm to room temperature. When the reaction was substantially complete, as indicated by TLC (1:1 hexanes/EtOAc), excess MeOH (20 mL) was added which resulted in the evolution of gas. The resulting mixture was diluted with Et$_2$O (50 mL) and aqueous NaHCO$_3$ (50 mL). The resulting layers were separated and the aqueous layer was extracted with Et$_2$O (2×50 mL). The combined organic extracts were washed with brine (50 mL), dried over anhydrous Na$_2$SO$_4$, filtered and then concentrated in vacuo to provide a reddish brown oil which solidified on standing. This material was purified using silica gel chromatography (5:1 hexanes/EtOAc) to provide a white solid.

Yield: 1.62 g (53%).

$^1$H NMR(DMSO-d$_6$): δ3.34 (s, 3H), 3.56–3.84 (m, 5H), 4.18–4.24 (dd, 1H, J=4.5, 3 Hz), 4.66 (s, 2H), 4.78 (s, 2H), 4.90 (d, 1H, J=1.5 Hz), 5.66 (s, 1H), 7.20–7.50 (m, 15H).

$^{13}$C NMR (DMSO-d$_6$): δ54.62, 62.09, 67.97, 71.74, 73.59, 77.49, 79.03, 80.87, 97.92, 100.26, 125.93, 127.21, 127.39, 127.54, 127.97, 128.01, 128.12, 128.69, 137.59, 138.36, 138.76;

MS (FD+): m/z 462.

B. Methyl-2,3,6-tri-O-benzyl-α-D-glucopyranoside

To a solution of Preparation 13A (1.62 g, 3.5 mmol) in THF (5 mL), was added 1M sodium cyanoborohydride in THF (36 mL, 36 mmol). A solution of Et$_2$O (10 mL) saturated with HCl gas was added slowly and the reaction flask was vented through a drying tube (the reaction mixture was pH 3). When the reaction was substantially complete, as indicated by TLC (1:1 hexanes/EtOAc), the mixture was diluted with Et$_2$O (50 mL) and aqueous NaHCO$_3$ (75 mL). The resulting layers were separated and the aqueous layer was extracted with Et$_2$O (2×30 mL). The combined organic extracts were dried over Na$_2$SO$_4$, filtered and then concentrated in vacuo to provide a viscous greenish-yellow oil. This oil was purified using silica gel chromatography (1:1 hexanes/EtOAc) to provide a colorless viscous oil.

Yield: 1.25 g (77%).

$^1$H NMR (CDCl$_3$): δ2.94 (br.s, 1H), 3.38 (s, 3H), 3.50–3.90 (m, 6H), 4.48–4.82 (m, 6H), 5.06 (d, 1H, J=3 Hz), 7.10–7.44 (m, 15H).

MS (FD+): m/z for C$_{28}$H$_{32}$O$_6$: Calcd: 464.5; Found: 463.1 (M-H).

Analysis for C$_{28}$H$_{32}$O$_6$: Calcd: C, 72.39; H, 6.94; Found: C, 72.02; H, 6.99.

EXAMPLE 1

4-Bromobenzyl methylphosphonate derivative of Preparation 9B

A solution of Preparation 9B (91% pure by HPLC, 5.3 g, 4.35 mmol) in DMF (13 mL) was added dropwise to a solution of lithium t-butoxide (t-BuOLi) (95% pure, 0.43 g, 5.13 mmol) in DMF (13 mL). The reaction mixture was stirred at room temperature until a dark brown solution formed. After cooling to 0° C., a solution of Preparation 6A (97.7% pure, 2.69 g, 5.13 mmol) in THF (26 mL) was added dropwise (0.4 mL/min). When the reaction was substantially complete, as indicated by HPLC (1–2% of Preparation 9B remained), the reaction was quenched by the addition of acetic acid (2 equiv. relative to the amount of base used). After 15 minutes, the mixture was poured into CH$_3$CN, resulting in the formation of a precipitate which was collected by filtration, dried in vacuo and redissolved in MeOH (10.5 mL). The resulting solution was poured into H$_2$O (133 mL) resulting in the formation of a precipitate and the mixture was stirred vigorously for 10 minutes and then filtered to provide 4.6 g (84% yield, corrected for 87.7% potency). This material was purified using silica gel chromatography (85:15 CH$_2$Cl$_2$/MeOH). R$_f$ 0.43 (90:10 CH$_2$Cl$_2$/MeOH).

IR(CHCl$_3$): 3338, 2937, 2876, 1639, 1609, 1529 cm$^{-1}$.

MS (FAB+) m/z 1356.

The reaction described in Example 1 was conducted with different combinations of solvents, base and amounts of reactants with the following results.

| Base (mol eq.) | Compound of Prep. 6A (mol e.g.) | Solvent | % Compound of Prep. 9B remaining | % Compound of Ex. 1 | % By-products |
|---|---|---|---|---|---|
| LiOH (2.2) | 1.5 | DMF | 15 | 74 | 3.0 |
| LiOH (1.0) | 2.0 | 2:3 DMF/THF | 23 | 74 | 0.1 |
| LiOH (1.05) | 2.0 | DMF | <1 | 95 | 1.5 |
| LiOH (2.2) | 2.0 | DMF | <1 | 80 | 16.0 |
| LiOTMS (1.1) | 1.1 | 1:1 DMF/THF | 5 | 89 | 1.5 |
| LiOTMS (1.3) | 1.2 | 1:1 DMF/THF | 3 | 90 | 1.7 |
| t-BuOLi (1.0) | 1.1 | 2:3 DMF/THF | 5 | 86 | 1.8 |
| t-BuOLi (1.18) | 1.18 | 1:1 DMF/THF | <1 | 94 | 1.0 |
| t-BuOLi (1.25) | 1.33 | 1:1 DMF/THF | <1 | 94 | 1.5 |

Reactions were run with 0.5–2.0 g of Preparation 9B. A 3M aqueous solution of LiOH was used. The percent (%) of Preparation 9B remaining was calculated using UV area percent by HPLC. The % by-products corresponds to the percent of late-eluting by-products by HPLC.

EXAMPLE 2

4-Bromobenzy methylphosphonate derivative of Preparation 9B

To 0.45 g (0.88 mmol) of one diastereomer of di-(4-bromobenzyl) dimethylpyrophosphonate prepared using the recrystallization described in Preparation 6B, was added 0.65 g (0.60 mmol) of Preparation 9B and 3 mL of DMF. The solution was cooled to −10° C. and 0.32 mL (0.64 mmol) of 2M aqueous LiOH was added over 1.5 h. The mixture was allowed to warm to 0° C. and an additional 0.12 mL of 2M LiOH was added. Acetic acid was added until the pH was 7 and the mixture was poured into 100 mL of CH$_3$CN. The resulting solid was collected by filtration,

EXAMPLE 3

Phosphonic Acid derivative of Preparation 9B

Example 1 (97% pure, 100 mg, 0.08 mmol) was hydrogenated using 10% Pd/C (50 mg), $Et_3N$ (0.03 mL, 0.22 mmol) in 90:10 THF/DMF (1.5 mL), under 1 atm of $H_2$. After 3 h, the mixture was filtered through celite and rinsed with THF (10 mL). The filtrate was concentrated in vacuo to provide a residue which was triturated with MeCN (10 mL) and then filtered to provide a white solid. This solid was rinsed with $Et_2O$ (2×3 mL) to provide 65 mg (74%) of crude material which was purified using HPLC chromatography.

IR (KBr): 3369, 2933,1634,1507,1436 $cm^{-1}$.

HRMS ($FAB^+$) m/z for $C_{58}H_{77}N_7O_{17}P$: Calcd: 1186.5114. Found: 1186.5139.

EXAMPLE 4

Benzyl methylphosphonate derivative of Preparation 9B

A solution of 2.4 g (2.17 mmol) of Preparation 9B in 8 mL of DMF was added to 1.54 g (4.35 mmol) of Preparation 7 and rinsed with 2 mL of DMF. The mixture was cooled to −10° C. and 1.4 mL (4.2 mmol) of 3M aqueous LiOH was added over 1 h. After an additional 30 minutes, 8.5 mmol of acetic acid was added and the reaction mixture was poured into 150 mL of cold $CH_3CN$. The resultant slurry was filtered and the solid was dried in vacuo to provide 1.9 g of material which was 87 area % of the phosphonate by HPLC. Purification of this material on silica gel using 14% MeOH and 1% acetic acid in $CH_2Cl_2$ provided the titled compound which was 94 area % by HPLC.

EXAMPLE 5

Phosphonic Acid Derivative of Preparation 9B

To a solution of 0.36 g of silica gel purified phosphonate from Example 4 in 2 mL of THF and 0.5 mL of $H_2O$ was added 0.06 g of 10% Pd/C in 1 mL of THF. After stirring for 2.5 h under $H_2$, the mixture was filtered. The filtrate was concentrated to provide 0.27 g (83%) of a solid. HPLC analysis showed that the product was the same as that isolated in Example 3 with a purity of 92 area %.

EXAMPLE 6

4-Bromobenzyl methylphosphonate derivative of diacetone-D-glucose

Diacetone-D-glucose (3.48 g, 1.31 mmol, 98% pure) in THF (15 mL) was slowly added to a solution of t-BuOLi (1.325 g, 1.57 mmol, 95% pure) in THF (20 mL) at 0° C. After 10 minutes, a solution of Preparation 6A (8.239 g, 1.57 mmol) in THF (75 mL) was added slowly while maintaining a temperature of 0–5° C. The resulting mixture was allowed to warm to room temperature and stirred for 20 h. When the reaction was substantially complete, as indicated by HPLC (consumption of the alcohol), the mixture was diluted with $Et_2O$ (50 mL) and aqueous $NaHCO_3$ (50 mL). The resulting layers were separated and the aqueous layer was extracted with $Et_2O$ (2×50 mL). The combined organic layers were washed with brine (100 mL), dried over $Na_2SO_4$, filtered and then concentrated in vacuo to provide a viscous yellow oil. This oil was determined to be a mixture of diastereomers and was purified using silica gel chromatography (75:25 EtOAc/hexanes).

Yield: 5.62 g (85%) of a white solid.

IR ($CHCl_3$): 2995,1250 $cm^{-1}$.

$^1$H NMR (DMSO-$d_6$): δ1.18 (s, 3H), 1.24 (s, 3H), 1.36 (s, 3H), 1.42 (s, 3H), 1.58–1.66 (d, 3H, J=10 Hz), 3.78–3.82 (m, 1H), 3.96–4.06 (m, 2H), 4.10–4.22 (m, 1H), 4.70–4.78 (m, 2H), 4.98–5.08 (m, 2H), 5.92 (d, 1H, J=3 Hz), 7.36–7.40 (d, 2H, J=6 Hz), 7.60–7.64 (d, 2H, J=6 Hz).

$^{13}$C NMR (DMSO-$d_6$): δ10.16, 12.03, 24.97, 25.93, 26.44, 65.37, 66.15, 71.62, 77.32, 79.76, 83.11, 104.44, 108.40, 111.32, 121.20, 129.54, 131.32, 136.00.

MS (FD+): m/z 506.9.

The following Examples 7–10 were prepared substantially in accordance with the procedure detailed in Example 6, using the designated starting material.

EXAMPLE 7

4-Bromobenzyl methylphosphonate derivative of Preparation 10B

IR ($CHCl_3$): 2932, 1251 $cm^{-1}$.

$^1$H NMR ($CDCl_3$): δ0.10 (s, 6H), 0.84 (s, 9H), 1.26 (s, 3H), 1.44 (s, 3H), 1.58 (d, 3H, J=10 Hz), 3.36 (s, 3H), 3.48 (q, 1H, J=3 Hz), 3.64 (q, 1H, J=3 Hz), 3.80 (d, 1H, J=6 Hz), 4.12 (d, 2H, J=3 Hz), 4.20 (m, 2H), 4.90 (s, 1H), 4.92–5.08 (m, 2H), 7.18 (d, 2H, J=6 Hz), 7.58 (d, 2H, J=6 Hz);

$^{13}$C NMR (DMSO-$d_6$): δ0.00, 10.53, 12.39, 17.81, 25.60, 26.15, 27.44, 53.99, 61.81, 64.73, 68.73, 72.99, 75.30, 76.55, 96.99, 109.10, 121.16, 129.44, 131.30, 136.02, 169.01.

MS (FD+): m/z 596.0.

EXAMPLE 8

4-Bromobenzyl methylphosphonate derivative of Preparation 11

IR ($CHCl_3$): 2934, 1249 $cm^{-1}$.

$^1$H NMR (DMSO-$d_6$): δ0.96 (s, 9H), 1.32 (s, 3H), 1.46 (s, 3H), 1.56–1.60 (d, 3H, J=10 Hz), 3.38 (s, 3H), 3.64–3.82 (m, 2H), 3.96 (d, 1H, J=6 Hz), 4.06–4.14 (m, 2H), 4.24–4.40 (q, 1H, J=4.5 Hz), 4.58–4.68 (dd, 1H, J=6, 1.5 Hz), 4.78–4.86 (dd, 1H, J=6, 1.5 Hz), 5.04 (s, 1H), 7.12–7.20 (d, 2H, J=6 Hz), 7.48 (m, 5 H), 7.58 (d, 2H, J=6 Hz), 7.60–7.72 (m, 5H).

$^{13}$C NMR (DMSO-$d_6$): δ10.58, 12.44, 18.69, 26.15, 26.38, 27.45, 54.00, 59.29, 62.58, 64.50, 68.60, 73.09, 75.31, 76.46, 97.01, 109.14, 121.16, 127.67, 127.74, 129.48, 129.74, 131.22, 132.56, 132.82, 135.01, 168.99.

MS (FD+): m/z 720.

Analysis for $C_{34}H_{44}O_8BrPSi$: Calcd: C, 56.74; H, 6.16; Found: C, 56.53; H, 6.22.

EXAMPLE 9

4-Bromobenzyl methylphosphonate derivative of Preparation 12C $^1$H NMR($CDCl_3$): δ1.40–1.44 (d, 3H, J=10 Hz), 1.84 (d, 6H, J=3 Hz), 3.60 (s, 3H), 3.86–3.96 (m, 1H), 4.24–4.58 (m, 4H), 4.82–5.16 (m, 5H), 5.34–5.42 (t, 1H, J=6 Hz), 7.06–7.30 (m, 7H), 7.40–7.48 (m, 2H).

MS (FD+): m/z 615.

Analysis for $C_{26}H_{32}O_{10}BrP$: Calcd: C, 50.74; H, 5.24; Found: C, 50.74; H, 5.31.

EXAMPLE 10

4-Bromobenzyl methylphosphonate derivative of Preparation 13B $^1$H NMR (DMSO-d$_6$): δ1.38–1.42 (d, 3H, J=12 Hz), 3.36 (s, 3H), 3.52–3.82 (m, 6H), 4.18–4.36 (m, 1H), 4.42 (d, 1H, J=3 Hz), 4.52 (d, 1H, J=1.5 Hz), 4.60–5.00 (m, 6H), 7.12 (d, 1H, J=6 Hz), 7.18–7.40 (m, 16H), 7.44 (d, 1H, J=6 Hz), 7.56 (d, 1H, J=6 Hz).

$^{13}$C NMR (DMSO-d$_6$): 610.96, 12.50, 54.86, 65.52, 68.77, 69.44, 71.61, 72.55, 73.86, 79.17, 79.39, 96.77, 121.20, 127.59, 127.66, 127.72, 127.78, 127.88, 128.19, 128.34, 129.61, 131.42, 131.56, 138.51,138.74.

MS (FD+): m/z 711.5.

EXAMPLE 11

4-Bromobenzyl methyl phosphonate derivative of (1R, 2S, 5R)-(–)-menthol (Mixture of isomers)

To the alcohol (1 equiv.) in anhydrous THF (10–20 mL/g of alcohol), was added t-BuOLi (1.1 eq.) in one portion. After cooling this mixture to 0° C., a solution of Preparation 6A (1.1 eq.) in THF/(7–10 mL/g Preparation 6A) was slowly added dropwise. When the reaction was substantially complete, as indicated by TLC, excess 1N HCl was added and the resulting mixture was combined with EtCAc in a separatory funnel. The resulting layers were separated and the organic layer was washed sequentially with a 1:1 mixture of brine and aqueous NaHCO$_3$, brine, and then dried over Na$_2$SO$_4$, filtered, and dried to provide crude material which was purified by silica gel chomatography.

IR (CHCl$_3$): 1490,1222, 995 cm$^{-1}$.

$^1$H NMR(CDCl$_3$): δ0.75 and 0.82 (d, 3H, J=7 Hz), 0.86 (m, 6H), 1.18 (m, 5H), 1.44 and 1.50 (d, 3H, J=3 Hz), 1.66 (br.d, 2H, J=11 Hz), 2.07 and 2.21 (m, 2H), 4.21 (m, 1H), 5.00 (m, 2H), 7.25 (d, 2H, J=8 Hz), 7.49 (d, 2H, J=8 Hz).

$^{13}$C NMR (CDCl$_3$): δ11.02, 12.03, 12.96, 13.96, 15.70, 20.93, 21.95, 22.85, 22.89, 25.56, 25.84, 31.50, 34.03, 43.11, 43.43, 48.39, 48.48, 65.81, 65.89, 66.02, 66.10, 122.31, 122.37, 129.44, 129.50, 131.37, 131.71, 135.63, 135.66, 135.71, 135.76.

MS (FD+): m/z 402 ($^{79}$Br), 404 ($^{81}$Br).

Analysis for C$_{18}$H$_{28}$O$_3$PBr: Calcd: C, 53.61; H, 7.00; Found: C, 53.84; H, 7.04.

The following Examples 12 and 13 were prepared substantially in accordance with the procedure detailed in Example 11.

EXAMPLE 12

4-Bromobenzyl methyl phosphonate derivative of 4-methoxyphenol

IR(CHCl$_3$): 1505, 1200, 941 cm$^{-1}$.

$^1$H NMR(CDCl$_3$): δ1.62 (d, 3H, J=17 Hz), 3.78 (s, 3), 5.05 (m, 2H), 6.82 (d, 2H, J=9 Hz), 7.07 (dd, 2H, J=1, 10 Hz), 7.21 (d, 2H, J=8 Hz), 7.46 (d, 2H, J=8 Hz).

$^{13}$C NMR (CDCl$_3$): δ10.53, 12.45, 55.62, 66.85, 66.94, 114.72, 121.40, 121.45, 122.53, 129.67, 131.75, 135.07, 135.15, 143.69, 156.81.

MS (FD+): m/z 370 ($^{79}$Br), 372 ($^{81}$Br).

EXAMPLE 13

4-Bromobenzyl methylphosphonate derivative of 1-phenyl-ethanol (mixture of isomers)

IR (CHCl$_3$): 1490, 1312, 974 cm$^{-1}$.

$^1$H NMR (CDCl$_3$): δ1.32 and 1.52 (d, 3H, J=17 Hz), 1.60 (dd, 3H, J=1, 6 Hz), 4.54 and 4.78 (dd, 1H, J=8, 12 Hz), 4.94 and 5.05 (dd, 1H, J=8 Hz, 12 Hz), 5.52 (m, 1H), 7.00 and 7.23 (d, 2H, J=8 Hz), 7.36 (m, 6H), 7.50 (d, 1H, J=8 Hz).

$^{13}$C NMR (CDCl$_3$): δ11.12, 11.34, 13.02, 3.27, 24.47, 24.53, 24.63, 24.70, 65.71, 65.80, 65.83, 65.91, 74.75, 74.83, 75.13, 75.21, 122.17, 122.36, 125.90, 128.18, 128.24, 128.59, 128.63, 129.27, 129.50, 131.57, 131.72, 135.50, 141.77, 142.00.

Analysis for C$_{16}$H$_{18}$O$_3$PBr: Calcd: C, 52.05; H, 4.91; Found: C, 51.78; H,4.84.

EXAMPLE 14

Phosphonic acid derivative of Preparation 10B

Example 7 (0.48 g, 0.80 mmol) was hydrogenated using 10% Pd/C (50 mg), Et$_3$N (0.2 mL, 1.6 mmol) and 1 atm of H$_2$ in EtOAc (10 mL). After 3 h, the mixture was filtered through celite, rinsed with EtOAc (10 mL) and then concentrated in vacuo.

Yield: 0.32 g (100% yield) of a viscous oil.

$^1$H NMR (CDCl$_3$): δ–0.06 (s, 6H), 0.74 (s, 9H), 1.18 (s, 3H), 1.24–1.28 (d, 3H, J=10 Hz), 1.44 (s, 3H), 3.22 (s, 3H), 3.24 (m, 1H), 3.52–3.60 (m, 1H), 3.88–4.20 (m, 3H), 4.80 (s, 1H), 5.66 (br, 1H).

MS (FD+): m/z 427.4.

Analysis for C$_{17}$H$_{38}$O$_8$PSi: Calcd: C, 47.87; H, 8.27; Found: C, 47.52; H, 8.98.

The following reaction was carried out in order to compare the present phosphonylation process with the phosphonic acid dichloride process known in the art.

Phosphonic Acid Derivative of Preparation 9B

A cold (0° C.) solution of Preparation 9B (81% pure by UV, 2.3 g, 1.68 mmol) in anhydrous DMF (10 mL), under N$_2$, was treated dropwise with a 1M LiOTMS in CH$_2$Cl$_2$ (2.5 mL, 2.5 mmol). The mixture was stirred for 10 minutes, followed by the dropwise addition of a solution of MeP(O)Cl$_2$ (1.1 g, 8.2 mmol) in anhydrous THF (2 mL). The reaction was monitored by HPLC. After 10 minutes, HPLC showed 47%. starting material, 12% of the phosphonic acid, and other by-product peaks. The reaction mixture was warmed to room temperature and stirred for 1 h, followed by the addition of excess LiOTM4S (2.5 mL). The resulting mixture was stirred for 2 h and then quenched by the addition of H$_2$O (3 mL). The reaction mixture was diluted with CH$_3$CN (80 mL) which resulted in the formation of a precipitate which was collected by filtration, washed with CH$_3$CN, and dried in vacuo to provide 5 g of a white solid. HPLC analysis indicated 37% starting material and 25% of the phosphonic acid derivative of Preparation 9B. The desired compound was isolated by HPLC chromatography (HP20SS column by step gradient elution: solvent A—42:58 MeCN/0.1% HOAc at pH 5; solvent B—60:40 MeCN/0.1% HOAc at pH 5).

We claim:

1. A compound of formula I:

$$\text{(structure I: pyrophosphate with R, OCH}_2\text{R}^1\text{ groups on each P)}$$

where:

R is $C_1$–$C_6$ alkyl or phenyl;

$R^1$ is phenyl, naphthyl, cyclohexyl or a compound of the formula $$\text{(para-substituted phenyl with } R^{1a}\text{)}$$

where $R^{1a}$ is hydrogen, halo, trifluoromethyl, $C_1$–$C_6$ alkyl, $C_1$–$C_6$ alkoxy, hydroxy, cyano, nitro, protected amino, phenyl, benzyl or benzyloxy;

with the proviso that when $R^1$ is $$\text{(ortho-R}^{1a}\text{-phenyl) or (para-R}^{1a}\text{-phenyl)},$$

then $R^{1a}$ cannot be hydroxy, $C_1$–$C_6$ alkoxy or benzyloxy;

or a pharmaceutically acceptable salt thereof.

2. A compound according to claim 1 where:

R is $C_1$–$C_4$ alkyl;

$R^1$ is phenyl or a compound of the formula $$\text{(phenyl-R}^{1a}\text{)}$$

where $R^{1a}$ is hydrogen, halo, $C_1$–$C_6$ alkyl or $C_1$–$C_6$ alkoxy;

or a pharmaceutically acceptable salt thereof.

3. A compound according to claim 2 where:

R is methyl;

$R^1$ is phenyl or a compound of the formula $$\text{(phenyl-R}^{1a}\text{)}$$

where $R^{1a}$ is halo or hydrogen;

or a pharmaceutically acceptable salt thereof.

4. A compound according to claim 3 where:

$R^1$ is phenyl or a compound of the formula $$\text{(phenyl-R}^{1a}\text{)}$$

where $R^{1a}$ is bromo or hydrogen;

or a pharmaceutically acceptable salt thereof.

5. A compound of formula II $$\text{(structure II: echinocandin-type cyclic hexapeptide with phosphate ester)}$$

wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$, and $R^{y4}$ are independently hydroxy or hydrogen;

R is $C_1$–$C_6$ alkyl, phenyl or benzyl;

Z is —$CH_2$—$R^1$;

$R^1$ is phenyl, naphthyl, cyclohexyl or a compound of the formula $$\text{(phenyl-R}^{1a}\text{)}$$

where $R^{1a}$ is hydrogen, halo, trifluoromethyl, $C_1$–$C_6$ alkyl, $C_1$–$C_6$ alkoxy, hydroxy, cyano, nitro, protected amino, phenyl, benzyl or benzyloxy;

$R_2$ is acyl;
with the proviso that when $R^1$ is

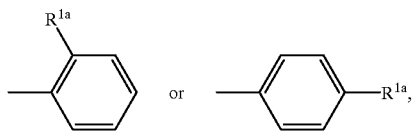

then $R^{1a}$ cannot be hydroxy, $C_1$–$C_6$ alkoxy or benzyloxy;
or a pharmaceutically acceptable salt thereof.

6. A compound according to claim 5 where:
$R'$, $R''$ and $R'''$ are each methyl;
$R^{x1}$ and $R^{x2}$ are independently hydrogen or hydroxy;
$R^{y1}$, $R^{y2}$, $R^{y3}$, and $R^{y4}$ are each hydroxy;
R is $C_1$–$C_4$ alkyl;
Z is —$CH_2$—$R^1$;
$R^1$ is phenyl, or a compound of the formula

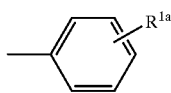

where $R^{1a}$ is hydrogen, halo, $C_1$–$C_6$ alkyl or $C_1$–$C_6$ alkoxy;

$R_2$ is an acyl group of the formula:

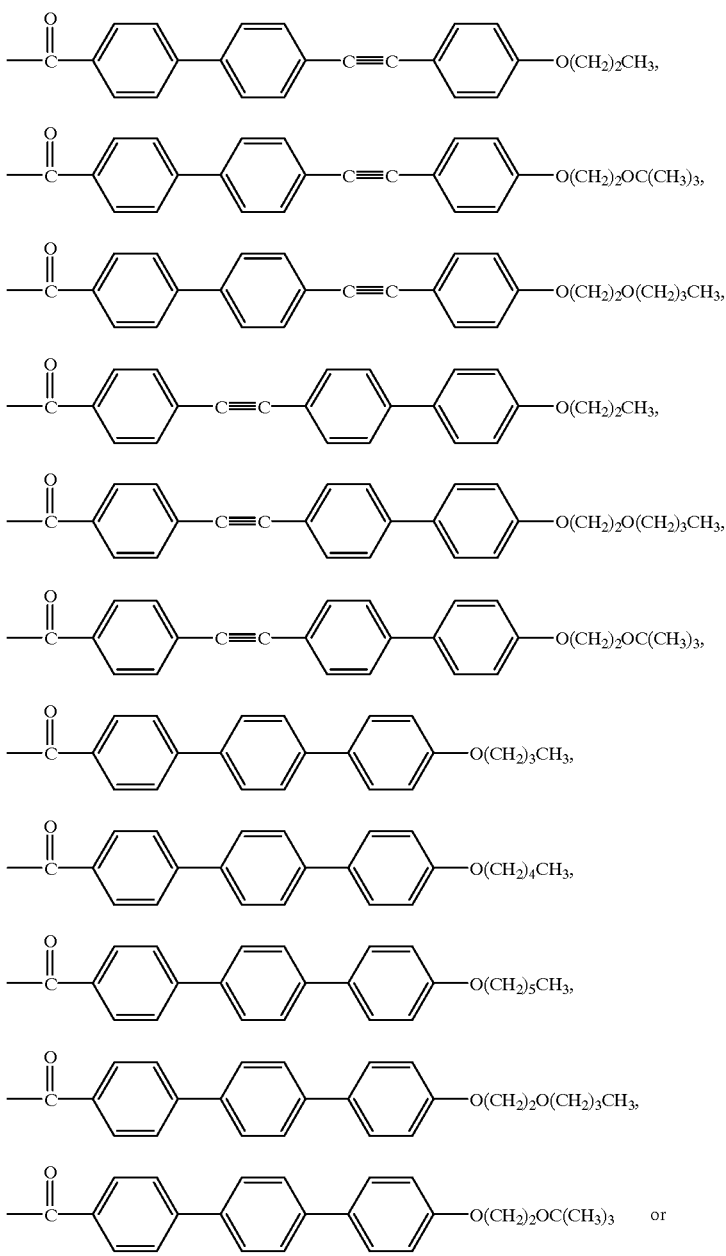

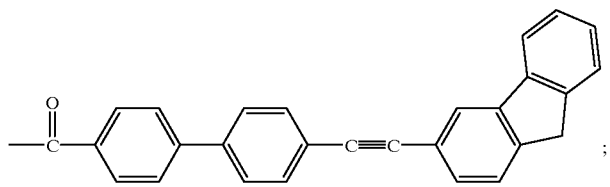

or a pharmaceutically acceptable salt thereof.

7. A compound according to claim 6 where:

R is methyl;

$R^1$ is phenyl or a compound of the formula

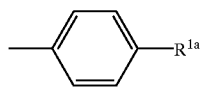

where $R^{1a}$ is halo or hydrogen;

or a pharmaceutically acceptable salt thereof.

8. A compound according to claim 7 where:

$R^1$ is phenyl or a compound of the formula

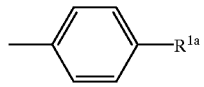

where $R^{1a}$ is bromo or hydrogen;

or a pharmaceutically acceptable salt thereof.

9. A compound according to claim 8 where:

$R_2$ is

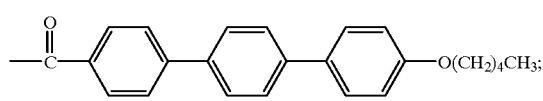

or a pharmaceutically acceptable salt thereof.

10. A process for preparing a compound of formula II

II wherein:

R' is hydrogen, methyl or $NH_2C(O)CH_2$—;

R" and R'" are independently methyl or hydrogen;

$R^{x1}$, $R^{x2}$, $R^{y1}$, $R^{y2}$, $R^{y3}$, and $R^{y4}$ are independently hydroxy or hydrogen;

R is $C_1$–$C_6$ alkyl, phenyl or benzyl;

Z is —$CH_2$—$R^1$;

$R^1$ is phenyl, naphthyl, cyclohexyl or a compound of the formula

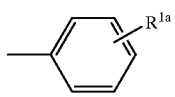

where $R^{1a}$ is hydrogen, halo, trifluoromethyl, $C_1$–$C_6$ alkyl, $C_1$–$C_6$ alkoxy, hydroxy, cyano, nitro, protected amino, phenyl, benzyl, or benzyloxy;

$R_2$ is an acyl side chain defined as

I) a group of the formula

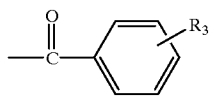

where:
- A) $R_3$ is $C_1$–$C_{12}$ alkyl, $C_1$–$C_6$ alkoxy or quinolyl;
- B) $R_3$ is —O—$(C_2)_m$—[O—$(CH)_n]_p$—O—$(C_1$–$C_{12}$ alkyl);
  m and n are independently 2, 3 or 4;
  p is 0 or 1; or
- C) $R_3$ is —Y—$(C_1$–$C_{12}$ alkyl);
  Y is —C≡C— or —CH=CH—; or
- D) $R_3$ is —O—$(CH_2)_q$—G;
  q is 2, 3 or 4;
  G is $C_7$–$C_{10}$ bicycloalkyl or $C_7$–$C_{14}$ tricycloalkyl; or II) a group of the formula

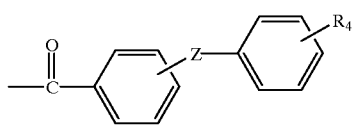

where:
Z is —O—, —C≡C—, —CH=CH—, —$CH_2$—$CH_2$—, —$CH_2$— or a bond;
- A) $R_4$ is hydrogen, $C_1$–$C_{12}$ alkyl, $C_1$–$C_{12}$ substituted alkyl, $C_2$–$C_{12}$ alkenyl, $C_2$–$C_{12}$ substituted alkenyl, $C_2$–$C_{12}$ alkynyl, $C_2$–$C_{12}$ substituted alkynyl, $C_1$–$C_{12}$ alkoxy, $C_3$–$C_{12}$ cycloalkyl, $C_7$–$C_{10}$ bicycloalkyl, $C_7$–$C_{14}$ tricycloalkyl, $C_3$–$C_{12}$ cycloalkoxy, naphthyl, pyridyl, thienyl, benzothienyl, quinolyl or phenyl; or
- B) $R_4$ is phenyl substituted by amino, $C_1$–$C_{12}$ alkylthio, halo, $C_1$–$C_{12}$ alkyl, $C_2$–$C_{12}$ alkenyl, $C_2$–$C_{12}$ alkynyl, $C_1$–$C_{12}$ substituted alkyl, $C_2$–$C_{12}$ substituted alkenyl, $C_2$–$C_{12}$ substituted alkynyl, $C_1$–$C_{12}$ alkoxy, trifluoromethyl, phenyl, substituted phenyl, or phenyl substituted with a group of the formula —O—$(CH_2)_m$—[O—$(CH_2)_n]_p$—O—$(C_1$–$C_{12}$ alkyl) where m, n and p are as defined above; or
- C) $R_4$ is $C_1$–$C_{12}$ alkoxy substituted with halo, $C_3$–$C_{12}$ cycloalkyl, $C_7$–$C_{10}$ bicycloalkyl, $C_7$–$C_{14}$ tricycloalkyl, $C_1$–$C_6$ alkoxy, $C_2$–$C_{12}$ alkynyl, amino, $C_1$–$C_4$ alkylamino, di($C_1$–$C_4$ alkyl)amino, formamido, $C_2$–$C_{12}$ alkanoylamino, or phenyl substituted with a group of the formula

where m, n and p are as defined above; or
- D) $R_4$ is —O—$(CH_2)_r$—W—$R_5$;
  r is 2, 3 or 4;
  W is pyrrolidino, piperidino or piperazino;
  $R_5$ is hydrogen, $C_1$–$C_{12}$ alkyl, $C_3$–$C_{12}$ cycloalkyl, benzyl or $C_3$–$C_{12}$ cycloalkylmethyl; or
- E) $R_4$ is —$Y^1$—$R_6$;
  $Y^1$ is —C≡C— or —CH=CH—;
  $R_6$ is $C_3$–$C_{12}$ cycloalkyl, $C_7$–$C_{10}$ bicycloalkyl, $C_7$–$C_{14}$ tricycloalkyl, $C_3$–$C_{12}$ cycloalkenyl, naphthyl, benzothiazolyl, thienyl, indanyl, fluorenyl, or phenyl substituted with $C_1$–$C_{12}$ alkylthio, $C_2$–$C_{12}$ alkenyl, $C_2$–$C_{12}$ alkynyl, halo($C_1$–$C_6$ alkoxy) or a group of the formula

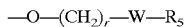

where r, W and $R_5$ are as defined above; or
$R_6$ is phenyl substituted with a group of the formula —O—$(CH_2)_m$—[O—$(CH_2)_n]_p$—O—$(C_1$–$C_{12}$ alkyl) where m, n and p are as defined above; or
- F) $R_4$ is $C_1$–$C_{12}$ alkoxy substituted with a group of the formula —NHC(O)$R_7$;
  $R_7$ is $C_1$–$C_6$ alkoxy, or phenyl($C_1$–$C_6$ alkoxy); or III) a group of the formula

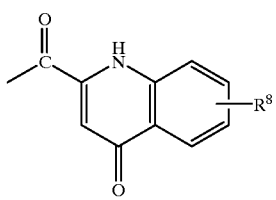

where:
$R^8$ is $C_1$–$C_{12}$ alkoxy or a group of the formula

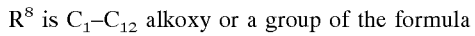

where m, n and p are as defined above; or

IV) a group of the formula

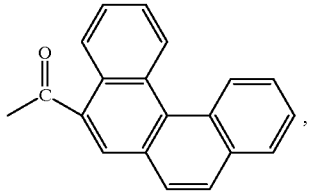

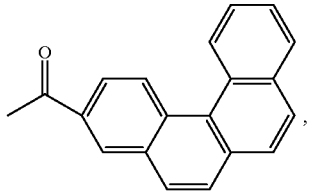

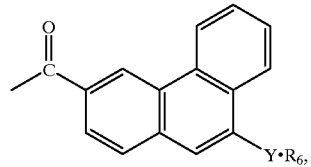

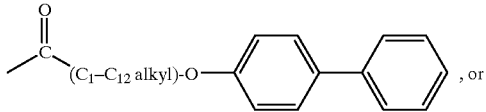, or

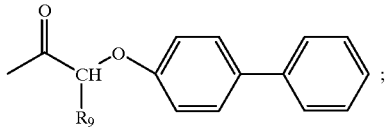;

where:

Y and $R_6$ are as defined above;

$R_9$ is phenyl $C_1$–$C_{12}$ alkyl, or $C_1$–$C_{12}$ alkoxy, or

V) naphthoyl substituted with $R_4$ where $R_4$ is as defined above;

with the proviso that when $R^1$ is

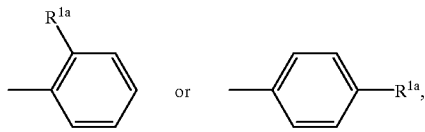

then $R^{1a}$ cannot be hydroxy, $C_1$–$C_6$ alkoxy or benzyloxy;

or a pharmaceutically acceptable salt thereof;

which comprises a) reacting a compound of formula I

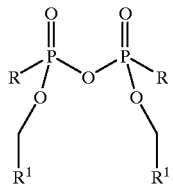

with a compound of formula IIB

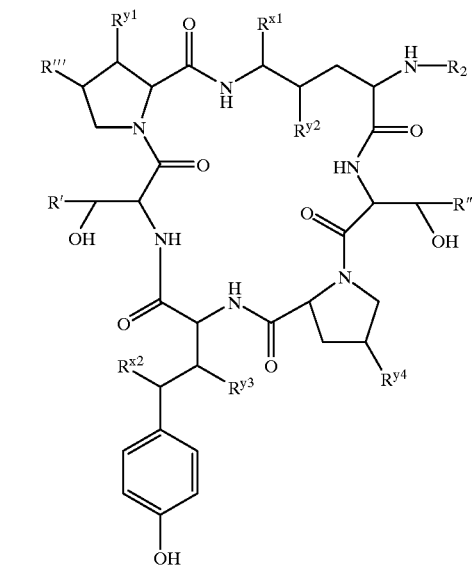

in the presence of a base at a temperature of from about −30° C. to about 40° C. to provide a compound of formula II;

b) optionally converting the compound of formula II to provide the compound of formula IIA where Z is hydrogen; and c) optionally forming a pharmaceutically acceptable salt.

11. A process according to claim 10 for preparing a compound of formula II where:
R', R'' and R''' are each methyl;
$R^{x1}$ and $R^{x2}$ are each hydrogen;
$R^{y1}$, $R^{y2}$, $R^{y3}$, and $R^{y4}$ are each hydroxy;
R is $C_1$–$C_4$ alkyl;
Z is —$CH_2$—$R^1$;
$R^1$ is phenyl, or a compound of the formula

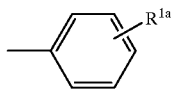

where $R^{1a}$ is hydrogen, halo, $C_1$–$C_6$ alkyl or $C_1$–$C_6$ alkoxy;
$R_2$ is an acyl group of the formula:

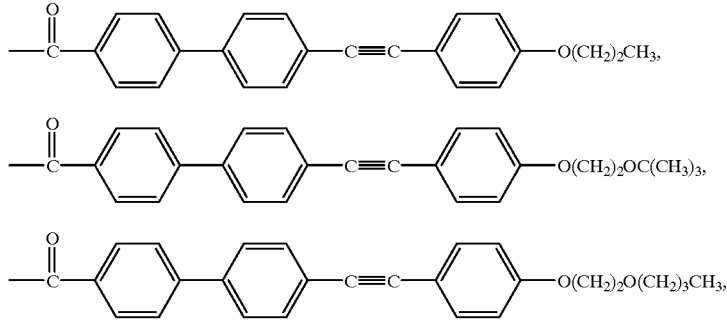

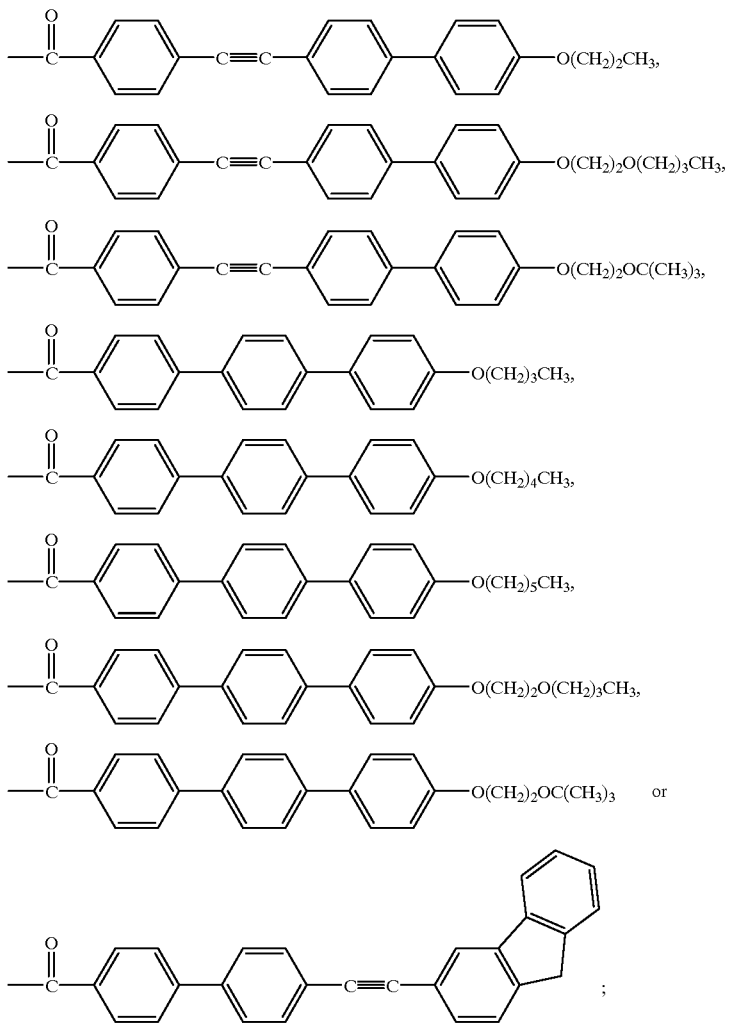

or a pharmaceutically acceptable salt thereof.

12. A process according to claim 11 for preparing a compound of formula II where:

R is methyl;

$R^1$ is phenyl or a compound of the formula

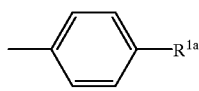

where $R^{1a}$ is halo or hydrogen;
or a pharmaceutically acceptable salt thereof.

13. A process according to claim 12 for preparing a compound of formula II where:

$R^1$ is phenyl or a compound of the formula

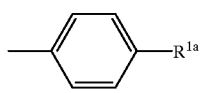

where $R^{1a}$ is bromo or hydrogen;
or a pharmaceutically acceptable salt thereof.

14. A process according to claim 13 for preparing a compound of formula II where:

$R_2$ is

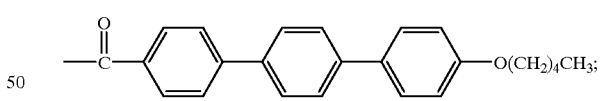

or a pharmaceutically acceptable salt thereof.

15. A process according to claim 10 which comprises reacting a compound of formula I where R is methyl and $R^1$ is phenyl or 4-bromophenyl.

16. A process according to claim 10 wherein the compound of formula I is a mixture of syn and anti diastereomers.

17. A process according to claim 15 wherein the compound of formula I is a mixture of syn and anti diastereomers.

18. A process according to claim 15 wherein the compound of formula I is the substantially purified syn or anti diastereomer.

19. A process for converting a compound of formula II:

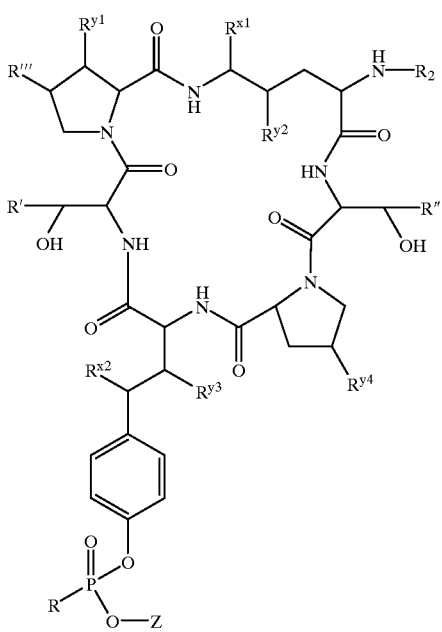

wherein:

R' is hydrogen, methyl or NH$_2$C(O)CH$_2$—;

R" and R'" are independently methyl or hydrogen;

R$^{x1}$, R$^{x2}$, R$^{y1}$, R$^{y2}$, R$^{y3}$, and R$^{y4}$ are independently hydroxy or hydrogen;

R is C$_1$–C$_6$ alkyl, phenyl or benzyl;

Z is —CH$_2$—R$^1$;

R$^1$ is phenyl, naphthyl, cyclohexyl or a compound of the formula

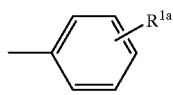

where R$^{1a}$ is hydrogen, halo, trifluoromethyl, C$_1$–C$_6$ alkyl, C$_1$–C$_6$ alkoxy, hydroxy, cyano, nitro, protected amino, phenyl, benzyl or benzyloxy;

R$_2$ is acyl;

with the proviso that when R$^1$ is

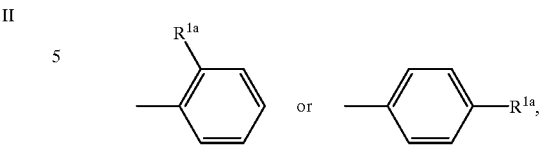

then R$^{1a}$ cannot be hydroxy, C$_1$–C$_6$ alkoxy or benzyloxy;

or a pharmaceutically acceptable salt thereof;

to a compound of formula IIA:

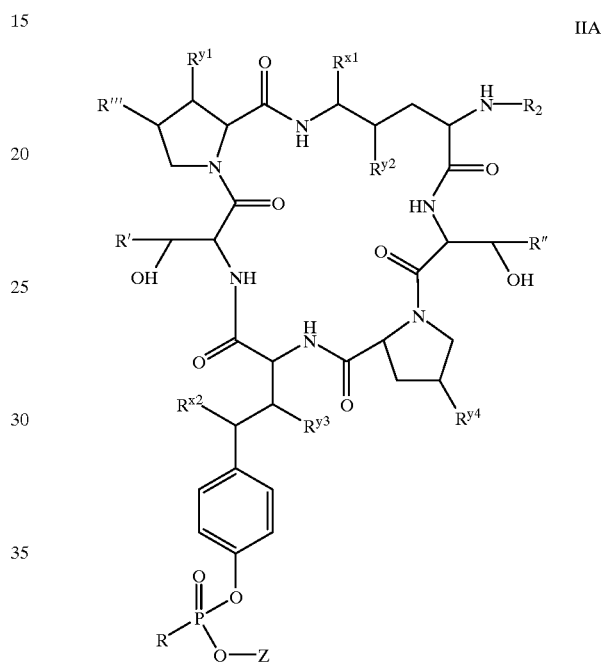

where:

R', R", R'", R$^{x1}$, R$^{x2}$, R$^{y1}$, R$^{y2}$, R$^{y3}$, R$^{y4}$, R and R$_2$ are as defined above; and Z is hydrogen, which comprises 1) hydrogenating the compound of formula II by
   a) exposure to hydrogen gas in the presence of a catalyst and a base; or
   b) reaction with an alkali metal in liquid ammonia; and
2) optionally forming a pharmaceutically acceptable salt.

20. The process according to claim 19 where the compound of formula II is hydrogenated by exposure to hydrogen gas where the catalyst is palladium or platinum on a solid support and the base is triethylamine, N-methyl morpholine, pyridine, or diisopropylethylamine.

21. The process according to claim 19 where the catalyst is palladium-on-carbon and the base is triethylamine.

* * * * *

UNITED STATES PATENT AND TRADEMARK OFFICE

CERTIFICATE OF CORRECTION

PATENT NO. : 6,043,341

DATED : March 28, 2000

INVENTOR(S) : UDODONG et al.

It is certified that error appears in the above-identified patent and that said Letters Patent is hereby corrected as shown below:

Claim 10, column 45, line 54, the compound should read: $-\text{O-(CH}_2)_m\text{-[O-(CH}_2)_n]_p\text{-O-(C}_1\text{-C}_{12}\text{ alkyl)}-$ Signed and Sealed this Twenty-seventh Day of February, 2001

Attest:

NICHOLAS P. GODICI

Attesting Officer

Acting Director of the United States Patent and Trademark Office